(12) United States Patent
Paddock et al.

(10) Patent No.: US 11,623,027 B2
(45) Date of Patent: Apr. 11, 2023

(54) PARTIALLY RESORBABLE IMPLANTS AND METHODS

(71) Applicant: Stryker European Operations Holdings LLC, Wilmington, DE (US)

(72) Inventors: Bradley William Paddock, Ridgewood, NJ (US); Amir Ali Sharifi-Mehr, Bloomingdale, NJ (US); Adam Laurance Wollowick, New York, NY (US); Oliver Buchert, Franklin Lakes, NJ (US); Matthew B. Havener, West Conshohocken, PA (US); Robert Cipoletti, Pompton Plains, NJ (US); Steven Willis, Mahwah, NJ (US); Marc Gilles Long, Denville, NJ (US)

(73) Assignee: Stryker European Operations Holdings LLC, Kalamazoo, MI (US)

( * ) Notice: Subject to any disclaimer, the term of this patent is extended or adjusted under 35 U.S.C. 154(b) by 525 days.

(21) Appl. No.: 16/720,968

(22) Filed: Dec. 19, 2019

(65) Prior Publication Data
US 2020/0121830 A1 Apr. 23, 2020

Related U.S. Application Data

(63) Continuation of application No. 15/158,202, filed on May 18, 2016, now Pat. No. 10,537,666.
(Continued)

(51) Int. Cl.
*A61L 27/58* (2006.01)
*A61F 2/44* (2006.01)
(Continued)

(52) U.S. Cl.
CPC ............... *A61L 27/58* (2013.01); *A61F 2/44* (2013.01); *A61F 2/447* (2013.01); *A61F 2/4465* (2013.01);
(Continued)

(58) Field of Classification Search
CPC .......... A61F 2/44; A61F 2/447; A61F 2/4465; A61L 27/58
See application file for complete search history.

(56) References Cited

U.S. PATENT DOCUMENTS

| 3,486,505 A | 12/1969 | Morrison |
| 3,641,590 A | 2/1972 | Michele |

(Continued)

FOREIGN PATENT DOCUMENTS

| CN | 203001182 U | 6/2013 |
| DE | 10052008 C1 | 8/2002 |

(Continued)

OTHER PUBLICATIONS

International Search Report and Written Opinion, PCT/US2010/22494, dated Oct. 25, 2010.
(Continued)

*Primary Examiner* — Christopher J Beccia
(74) *Attorney, Agent, or Firm* — Lerner, David, Littenberg, Krumholz & Mentlik, LLP

(57) ABSTRACT

Implants including non-resorbable frameworks and resorbable components, as well as methods of use thereof are disclosed. The embodiments include different combinations of a non-resorbable framework (in some case structural and in other cases non-structural), and a resorbable component embedded within and/or around the framework (again, in some cases structural and in other cases non-structural). The disclosed implants provide an efficient means of providing structural support for the vertebral bodies post-implantation, as well as encouraging resorption of the implant and fusion of the associated vertebral bodies without negative side effects and/or failure, such as subsidence of the implant or cracking/fracturing of a portion of the implant when implanted.

6 Claims, 23 Drawing Sheets
(8 of 23 Drawing Sheet(s) Filed in Color)

Related U.S. Application Data

(60) Provisional application No. 62/163,146, filed on May 18, 2015.

(51) Int. Cl.
  *A61F 2/30* (2006.01)
  *A61F 2/46* (2006.01)
  *A61L 27/50* (2006.01)

(52) U.S. Cl.
  CPC ..... *A61F 2/4455* (2013.01); *A61F 2002/3008* (2013.01); *A61F 2002/30032* (2013.01); *A61F 2002/30133* (2013.01); *A61F 2002/30235* (2013.01); *A61F 2002/30387* (2013.01); *A61F 2002/30677* (2013.01); *A61F 2002/30883* (2013.01); *A61F 2002/30884* (2013.01); *A61F 2002/30904* (2013.01); *A61F 2002/4629* (2013.01); *A61F 2002/4631* (2013.01); *A61L 27/50* (2013.01); *A61L 2430/38* (2013.01)

(56) References Cited

U.S. PATENT DOCUMENTS

| | | | |
|---|---|---|---|
| 3,852,045 A | 12/1974 | Wheeler et al. | |
| 3,855,638 A | 12/1974 | Pilliar | |
| 4,047,524 A | 9/1977 | Hall | |
| 4,501,269 A | 2/1985 | Bagby | |
| 4,612,160 A | 9/1986 | Donlevy et al. | |
| 4,653,489 A | 3/1987 | Tronzo | |
| 4,681,589 A | 7/1987 | Tronzo | |
| 4,718,914 A | 1/1988 | Frey et al. | |
| 4,743,262 A | 5/1988 | Tronzo | |
| 4,820,305 A | 4/1989 | Harms et al. | |
| 4,834,757 A | 5/1989 | Brantigan | |
| 4,946,378 A | 8/1990 | Hirayama et al. | |
| 5,071,437 A | 12/1991 | Steffee | |
| 5,156,628 A | 10/1992 | Kranz | |
| 5,180,381 A | 1/1993 | Aust et al. | |
| 5,192,327 A | 3/1993 | Brantigan | |
| 5,263,986 A | 11/1993 | Noiles et al. | |
| 5,306,309 A | 4/1994 | Wagner et al. | |
| 5,314,477 A | 5/1994 | Marnay | |
| 5,370,692 A | 12/1994 | Fink et al. | |
| 5,431,658 A | 7/1995 | Moskovich | |
| 5,443,514 A | 8/1995 | Steffee | |
| 5,443,515 A | 8/1995 | Cohen et al. | |
| 5,458,643 A | 10/1995 | Oka et al. | |
| 5,489,308 A | 2/1996 | Kuslich et al. | |
| 5,504,300 A | 4/1996 | Devanathan et al. | |
| 5,507,816 A | 4/1996 | Bullivant | |
| 5,514,180 A | 5/1996 | Heggeness et al. | |
| 5,609,635 A | 3/1997 | Michelson | |
| 5,672,284 A | 9/1997 | Devanathan et al. | |
| 5,683,394 A | 11/1997 | Rinner | |
| 5,702,449 A * | 12/1997 | McKay ................ C08L 89/00 623/17.16 |
| 5,702,455 A | 12/1997 | Saggar | |
| 5,709,683 A | 1/1998 | Bagby | |
| 5,713,899 A | 2/1998 | Marnay et al. | |
| 5,723,011 A | 3/1998 | Devanathan et al. | |
| 5,734,959 A | 3/1998 | Krebs et al. | |
| 5,768,134 A | 6/1998 | Swaelens et al. | |
| 5,776,199 A | 7/1998 | Michelson | |
| 5,885,299 A | 3/1999 | Winslow et al. | |
| 5,893,889 A | 4/1999 | Harrington | |
| 5,961,554 A | 10/1999 | Janson et al. | |
| 6,039,761 A | 3/2000 | Li et al. | |
| 6,039,762 A | 3/2000 | McKay | |
| 6,096,080 A | 8/2000 | Nicholson et al. | |
| 6,113,638 A | 9/2000 | Williams et al. | |
| 6,120,503 A | 9/2000 | Michelson | |
| 6,152,927 A | 11/2000 | Farris et al. | |
| 6,193,721 B1 | 2/2001 | Michelson | |
| 6,206,924 B1 | 3/2001 | Timm | |
| 6,235,059 B1 | 5/2001 | Benezech et al. | |
| 6,241,769 B1 | 6/2001 | Nicholson et al. | |
| 6,241,771 B1 | 6/2001 | Gresser et al. | |
| 6,293,949 B1 | 9/2001 | Justis et al. | |
| 6,325,805 B1 | 12/2001 | Ogilvie et al. | |
| 6,336,928 B1 | 1/2002 | Guerin et al. | |
| 6,364,880 B1 | 4/2002 | Michelson | |
| 6,371,987 B1 * | 4/2002 | Weiland ................ A61F 2/4455 623/17.11 |
| 6,432,107 B1 | 8/2002 | Ferree | |
| 6,447,524 B1 | 9/2002 | Knodel et al. | |
| 6,447,546 B1 | 9/2002 | Bramlet et al. | |
| 6,454,769 B2 | 9/2002 | Wagner et al. | |
| 6,458,158 B1 | 10/2002 | Anderson et al. | |
| 6,471,725 B1 | 10/2002 | Ralph et al. | |
| 6,485,521 B1 | 11/2002 | Say et al. | |
| 6,503,250 B2 | 1/2003 | Paul | |
| 6,533,786 B1 | 3/2003 | Needham et al. | |
| 6,533,818 B1 | 3/2003 | Weber et al. | |
| 6,547,823 B2 | 4/2003 | Scarborough et al. | |
| 6,569,201 B2 | 5/2003 | Moumene et al. | |
| 6,572,654 B1 | 6/2003 | Santilli | |
| 6,582,468 B1 | 6/2003 | Gauchet | |
| 6,623,525 B2 | 9/2003 | Ralph et al. | |
| 6,673,075 B2 | 1/2004 | Santilli | |
| 6,679,887 B2 | 1/2004 | Nicholson et al. | |
| 6,716,245 B2 | 4/2004 | Pasquet et al. | |
| 6,726,720 B2 | 4/2004 | Ross et al. | |
| 6,740,118 B2 | 5/2004 | Eisermann et al. | |
| 6,740,186 B2 | 5/2004 | Hawkins et al. | |
| 6,743,256 B2 | 6/2004 | Mason | |
| 6,767,367 B1 | 7/2004 | Michelson | |
| 6,790,233 B2 | 9/2004 | Brodke et al. | |
| 6,800,093 B2 | 10/2004 | Nicholson et al. | |
| 6,843,805 B2 | 1/2005 | Webb et al. | |
| 6,863,689 B2 | 3/2005 | Ralph et al. | |
| 6,890,335 B2 | 5/2005 | Grabowski et al. | |
| 6,890,355 B2 | 5/2005 | Michelson | |
| 6,945,448 B2 | 9/2005 | Medlin et al. | |
| 6,970,233 B2 | 11/2005 | Blatchford | |
| 7,018,416 B2 * | 3/2006 | Hanson ............... A61B 17/1671 623/17.16 |
| 7,044,972 B2 * | 5/2006 | Mathys, Jr ............ A61F 2/4455 623/17.11 |
| 7,048,766 B2 | 5/2006 | Ferree | |
| 7,056,344 B2 | 6/2006 | Huppert et al. | |
| 7,056,345 B2 | 6/2006 | Kuslich | |
| 7,060,097 B2 | 6/2006 | Fraser et al. | |
| 7,118,580 B1 | 10/2006 | Beyersdorff et al. | |
| 7,128,761 B2 | 10/2006 | Kuras et al. | |
| 7,135,042 B2 | 11/2006 | Stoll | |
| 7,169,150 B2 | 1/2007 | Shipp et al. | |
| 7,204,852 B2 | 4/2007 | Marnay et al. | |
| 7,235,101 B2 | 6/2007 | Berry et al. | |
| 7,238,203 B2 | 7/2007 | Bagga et al. | |
| 7,241,313 B2 | 7/2007 | Unwin et al. | |
| 7,255,713 B2 | 8/2007 | Malek | |
| 7,278,997 B1 | 10/2007 | Mueller et al. | |
| 7,303,564 B2 | 12/2007 | Freid et al. | |
| 7,320,707 B2 | 1/2008 | Zucherman et al. | |
| 7,331,995 B2 | 2/2008 | Eisermann et al. | |
| 7,364,589 B2 | 4/2008 | Eisermann | |
| 7,497,876 B2 | 3/2009 | Tuke et al. | |
| 7,500,976 B2 | 3/2009 | Suh | |
| 7,501,073 B2 | 3/2009 | Wen et al. | |
| 7,503,934 B2 | 3/2009 | Eisermann et al. | |
| 7,503,935 B2 | 3/2009 | Zucherman et al. | |
| 7,537,664 B2 | 5/2009 | O'Neill et al. | |
| 7,563,284 B2 | 7/2009 | Coppes et al. | |
| 7,588,600 B2 | 9/2009 | Benzel et al. | |
| 7,594,931 B2 | 9/2009 | Louis et al. | |
| 7,611,538 B2 | 11/2009 | Belliard et al. | |
| 7,625,375 B2 | 12/2009 | Garden et al. | |
| 7,635,447 B2 | 12/2009 | Hamman et al. | |
| 7,658,766 B2 | 2/2010 | Melkent et al. | |
| 7,662,186 B2 | 2/2010 | Bagga et al. | |
| 7,670,359 B2 | 3/2010 | Yundt | |
| 7,670,375 B2 | 3/2010 | Schaller | |
| 7,695,516 B2 | 4/2010 | Zeegers | |

(56) References Cited

U.S. PATENT DOCUMENTS

| | | |
|---|---|---|
| 7,749,271 B2 | 7/2010 | Fischer et al. |
| 7,763,076 B2 | 7/2010 | Navarro et al. |
| 7,766,947 B2 | 8/2010 | Hawkes et al. |
| 7,842,088 B2 | 11/2010 | Rashbaum et al. |
| 7,857,839 B2 | 12/2010 | Duong et al. |
| 7,862,597 B2 | 1/2011 | Gause et al. |
| 7,883,661 B2 | 2/2011 | Hamman et al. |
| 7,896,919 B2 | 3/2011 | Belliard et al. |
| 7,918,382 B2 | 4/2011 | Charlebois et al. |
| 7,922,765 B2 | 4/2011 | Reiley |
| 8,021,403 B2 | 9/2011 | Wall et al. |
| 8,034,076 B2 | 10/2011 | Criscuolo et al. |
| 8,043,346 B2 | 10/2011 | Markworth |
| 8,083,796 B1 | 12/2011 | Raiszadeh et al. |
| 8,092,499 B1 | 1/2012 | Roth |
| 8,100,974 B2 | 1/2012 | Duggal et al. |
| 8,105,366 B2 | 1/2012 | Null et al. |
| 8,123,808 B2 | 2/2012 | Dewey et al. |
| 8,147,861 B2 | 4/2012 | Jones et al. |
| 8,167,946 B2 | 5/2012 | Michelson |
| 8,191,760 B2 | 6/2012 | Charlebois et al. |
| 8,202,305 B2 | 6/2012 | Reiley |
| 8,231,676 B2 | 7/2012 | Trudeau et al. |
| 8,236,034 B2 | 8/2012 | Binder et al. |
| 8,262,737 B2 | 9/2012 | Bagga et al. |
| 8,266,780 B2 | 9/2012 | Bollinger et al. |
| 8,268,100 B2 | 9/2012 | O'Neill et al. |
| 8,303,879 B2 | 11/2012 | Bertele et al. |
| 8,308,805 B2 | 11/2012 | Lynn et al. |
| 8,343,224 B2 | 1/2013 | Lynn et al. |
| 8,349,015 B2 | 1/2013 | Bae et al. |
| 8,361,126 B2 | 1/2013 | Perrow et al. |
| 8,361,150 B2 | 1/2013 | Zhang et al. |
| 8,361,153 B2 | 1/2013 | Ralph et al. |
| 8,361,380 B2 | 1/2013 | Hamman et al. |
| 8,388,667 B2 | 3/2013 | Reiley et al. |
| 8,403,969 B2 | 3/2013 | Wallenstein et al. |
| 8,403,991 B2 | 3/2013 | Ullrich, Jr. et al. |
| 8,414,648 B2 | 4/2013 | Reiley |
| 8,414,650 B2 | 4/2013 | Bertele et al. |
| 8,414,651 B2 | 4/2013 | Tyber et al. |
| 8,414,654 B1 | 4/2013 | Ganey |
| 8,414,820 B2 | 4/2013 | Bertele et al. |
| 8,419,777 B2 | 4/2013 | Walker et al. |
| 8,425,570 B2 | 4/2013 | Reiley |
| 8,425,604 B2 | 4/2013 | Trieu |
| 8,430,930 B2 | 4/2013 | Hunt |
| 8,435,301 B2 | 5/2013 | Gerber et al. |
| 8,435,302 B2 | 5/2013 | Ulrich, Jr. et al. |
| 8,444,693 B2 | 5/2013 | Reiley |
| 8,470,004 B2 | 6/2013 | Reiley |
| 8,470,042 B2 | 6/2013 | Zhang et al. |
| 8,480,749 B2 | 7/2013 | Ullrich, Jr. et al. |
| 8,486,115 B2 | 7/2013 | Fisher et al. |
| 8,496,710 B2 | 7/2013 | Bagga et al. |
| 8,500,782 B2 | 8/2013 | Kovach et al. |
| 8,500,811 B2 | 8/2013 | Blain et al. |
| 8,500,819 B2 | 8/2013 | Meridew et al. |
| 8,530,560 B2 | 9/2013 | Kerr et al. |
| 8,535,354 B2 | 9/2013 | Cummins |
| 8,545,568 B2 | 10/2013 | Ulrich, Jr. et al. |
| 8,551,173 B2 | 10/2013 | Lechmann et al. |
| 8,551,176 B2 | 10/2013 | Ullrich, Jr. et al. |
| 8,556,981 B2 | 10/2013 | Jones et al. |
| 8,562,684 B2 | 10/2013 | Ullrich, Jr. et al. |
| 8,562,685 B2 | 10/2013 | Ullrich, Jr. et al. |
| 8,585,765 B2 | 11/2013 | Ullrich, Jr. et al. |
| 8,585,766 B2 | 11/2013 | Ullrich, Jr. et al. |
| 8,585,767 B2 | 11/2013 | Ullrich, Jr. et al. |
| 8,591,590 B2 | 11/2013 | Ullrich, Jr. et al. |
| 8,617,246 B2 | 12/2013 | Malone |
| 8,617,248 B2 | 12/2013 | Ullrich, Jr. et al. |
| 8,632,604 B2 | 1/2014 | Brooks |
| 8,636,803 B2 | 1/2014 | Hibri et al. |
| 8,663,332 B1 | 3/2014 | To et al. |
| 8,673,016 B2 | 3/2014 | Liu |
| 8,709,088 B2 | 4/2014 | Kleiner et al. |
| 8,734,462 B2 | 5/2014 | Reiley et al. |
| 8,747,412 B2 | 6/2014 | Bae et al. |
| 8,758,442 B2 | 6/2014 | Ullrich, Jr. et al. |
| 8,758,443 B2 | 6/2014 | Ullrich, Jr. et al. |
| 8,814,939 B2 | 8/2014 | Ullrich, Jr. et al. |
| 8,814,978 B2 | 8/2014 | Hamman et al. |
| 8,821,555 B2 | 9/2014 | Bae et al. |
| 8,827,986 B2 | 9/2014 | Shachar et al. |
| 8,834,571 B2 | 9/2014 | Bagga et al. |
| 8,840,623 B2 | 9/2014 | Reiley |
| 8,845,736 B2 | 9/2014 | Zhang et al. |
| 8,864,831 B2 | 10/2014 | Lee et al. |
| 8,900,277 B2 | 12/2014 | Perrow et al. |
| 8,906,093 B2 | 12/2014 | Malone |
| 8,906,095 B2 | 12/2014 | Christensen et al. |
| 8,940,053 B2 | 1/2015 | Ullrich, Jr. et al. |
| 8,979,934 B2 | 3/2015 | Kirschman |
| 8,985,430 B2 | 3/2015 | Charlebois et al. |
| 8,992,619 B2 | 3/2015 | Patterson et al. |
| 9,060,876 B1 | 6/2015 | To et al. |
| 9,078,718 B2 | 7/2015 | Campbell |
| 9,089,428 B2 | 7/2015 | Bertele et al. |
| 9,135,374 B2 | 9/2015 | Jones et al. |
| 9,180,010 B2 | 11/2015 | Dong et al. |
| 9,320,549 B2 | 4/2016 | Fraser et al. |
| 9,375,237 B2 | 6/2016 | Keegan et al. |
| 9,381,044 B2 | 7/2016 | Robinson et al. |
| 9,387,087 B2 | 7/2016 | Tyber |
| 9,615,733 B2 | 4/2017 | Nottmeier |
| 9,629,664 B2 | 4/2017 | Altarac et al. |
| 9,655,665 B2 | 5/2017 | Perrow |
| 9,730,807 B2 | 8/2017 | Donaldson |
| 9,782,270 B2 | 10/2017 | Wickham |
| 9,925,051 B2 | 3/2018 | Bae et al. |
| 10,070,970 B2 | 9/2018 | Lynn et al. |
| 10,537,666 B2 * | 1/2020 | Paddock .................. A61F 2/44 |
| 10,695,192 B2 * | 6/2020 | Bishop ................ A61F 2/30771 |
| 2002/0004683 A1 | 1/2002 | Michelson |
| 2002/0035400 A1 | 3/2002 | Bryan et al. |
| 2002/0165613 A1 | 11/2002 | Lin et al. |
| 2003/0045940 A1 | 3/2003 | Eberlein et al. |
| 2003/0055505 A1 | 3/2003 | Sicotte et al. |
| 2003/0083748 A1 | 5/2003 | Lee et al. |
| 2003/0195517 A1 | 10/2003 | Michelson |
| 2003/0195632 A1 | 10/2003 | Foley et al. |
| 2004/0059318 A1 | 3/2004 | Zhang et al. |
| 2004/0082999 A1 | 4/2004 | Mathys et al. |
| 2004/0117022 A1 | 6/2004 | Marnay et al. |
| 2004/0122426 A1 | 6/2004 | Michelson |
| 2004/0133279 A1 | 7/2004 | Krueger et al. |
| 2004/0148028 A1 | 7/2004 | Ferree et al. |
| 2004/0176853 A1 | 9/2004 | Sennett et al. |
| 2004/0181226 A1 | 9/2004 | Michelson |
| 2004/0193269 A1 | 9/2004 | Fraser et al. |
| 2004/0193271 A1 | 9/2004 | Fraser et al. |
| 2004/0199254 A1 | 10/2004 | Louis et al. |
| 2004/0204712 A1 | 10/2004 | Kolb et al. |
| 2004/0210218 A1 | 10/2004 | Dixon et al. |
| 2004/0215195 A1 | 10/2004 | Shipp et al. |
| 2004/0220566 A1 | 11/2004 | Bray |
| 2004/0220571 A1 | 11/2004 | Assaker et al. |
| 2004/0220668 A1 | 11/2004 | Eisermann et al. |
| 2004/0220670 A1 | 11/2004 | Eisermann et al. |
| 2004/0225360 A1 | 11/2004 | Malone |
| 2004/0230307 A1 | 11/2004 | Eisermann |
| 2004/0258732 A1 | 12/2004 | Shikinami |
| 2004/0260286 A1 | 12/2004 | Ferree |
| 2005/0004672 A1 | 1/2005 | Pafford et al. |
| 2005/0033294 A1 | 2/2005 | Garden et al. |
| 2005/0033435 A1 | 2/2005 | Belliard et al. |
| 2005/0043802 A1 | 2/2005 | Eisermann et al. |
| 2005/0049593 A1 | 3/2005 | Duong et al. |
| 2005/0049595 A1 | 3/2005 | Suh et al. |
| 2005/0060034 A1 | 3/2005 | Berry et al. |
| 2005/0070900 A1 | 3/2005 | Serhan et al. |
| 2005/0075633 A1 | 4/2005 | Ross |
| 2005/0123672 A1 | 6/2005 | Justin et al. |

(56) References Cited

U.S. PATENT DOCUMENTS

| | | |
|---|---|---|
| 2005/0143820 A1 | 6/2005 | Zucherman et al. |
| 2005/0149192 A1 | 7/2005 | Zucherman et al. |
| 2005/0149193 A1 | 7/2005 | Zucherman et al. |
| 2005/0154460 A1 | 7/2005 | Yundt |
| 2005/0165408 A1 | 7/2005 | Puno et al. |
| 2005/0177238 A1 | 8/2005 | Khandkar et al. |
| 2005/0192586 A1 | 9/2005 | Zucherman et al. |
| 2005/0216081 A1 | 9/2005 | Taylor |
| 2006/0004453 A1 | 1/2006 | Bartish et al. |
| 2006/0036250 A1 | 2/2006 | Lange et al. |
| 2006/0085071 A1 | 4/2006 | Lechmann et al. |
| 2006/0089656 A1 | 4/2006 | Allard et al. |
| 2006/0116769 A1 | 6/2006 | Marnay et al. |
| 2006/0116770 A1 | 6/2006 | White et al. |
| 2006/0122603 A1 | 6/2006 | Kolb |
| 2006/0129238 A1 | 6/2006 | Paltzer |
| 2006/0136063 A1 | 6/2006 | Zeegers |
| 2006/0147332 A1 | 7/2006 | Jones et al. |
| 2006/0178745 A1 | 8/2006 | Bartish et al. |
| 2006/0195097 A1 | 8/2006 | Evans et al. |
| 2006/0212121 A1 | 9/2006 | Ferree |
| 2006/0293668 A1 | 12/2006 | May et al. |
| 2007/0050032 A1 | 3/2007 | Gittings et al. |
| 2007/0050033 A1 | 3/2007 | Reo et al. |
| 2007/0055378 A1 | 3/2007 | Ankney et al. |
| 2007/0073404 A1 | 3/2007 | Rashbaum et al. |
| 2007/0118145 A1 | 5/2007 | Fischer et al. |
| 2007/0123884 A1 | 5/2007 | Abdou |
| 2007/0123985 A1 | 5/2007 | Errico et al. |
| 2007/0142914 A1 | 6/2007 | Jones et al. |
| 2007/0173816 A1 | 7/2007 | Metz-Stavenhagen |
| 2007/0173940 A1 | 7/2007 | Hestad et al. |
| 2007/0179609 A1 | 8/2007 | Goble et al. |
| 2007/0233244 A1 | 10/2007 | Lopez et al. |
| 2007/0233261 A1 | 10/2007 | Lopez et al. |
| 2007/0239278 A1 | 10/2007 | Heinz |
| 2007/0270968 A1 | 11/2007 | Baynham et al. |
| 2008/0004709 A1 | 1/2008 | O'Neill et al. |
| 2008/0015702 A1 | 1/2008 | Lakin et al. |
| 2008/0051901 A1 | 2/2008 | de Villiers et al. |
| 2008/0051902 A1 | 2/2008 | Dwyer |
| 2008/0097435 A1 | 4/2008 | DeRidder et al. |
| 2008/0109005 A1 | 5/2008 | Trudeau et al. |
| 2008/0154377 A1 | 6/2008 | Voellmicke |
| 2008/0161927 A1 | 7/2008 | Savage et al. |
| 2008/0183292 A1 | 7/2008 | Trieu |
| 2008/0249575 A1 | 10/2008 | Waugh et al. |
| 2008/0262623 A1 | 10/2008 | Bagga et al. |
| 2008/0269756 A1 | 10/2008 | Tomko et al. |
| 2008/0306595 A1 | 12/2008 | McLeod et al. |
| 2009/0005870 A1 | 1/2009 | Hawkins et al. |
| 2009/0088849 A1 | 4/2009 | Armstrong et al. |
| 2009/0093885 A1 | 4/2009 | Levieux et al. |
| 2009/0105832 A1 | 4/2009 | Allain et al. |
| 2009/0112323 A1 | 4/2009 | Hestad et al. |
| 2009/0138015 A1 | 5/2009 | Conner et al. |
| 2009/0157187 A1 | 6/2009 | Richelsoph |
| 2009/0164020 A1 | 6/2009 | Janowski et al. |
| 2009/0198184 A1 | 8/2009 | Martin et al. |
| 2009/0240333 A1 | 9/2009 | Trudeau et al. |
| 2009/0240334 A1 | 9/2009 | Richelsoph |
| 2009/0287257 A1 | 11/2009 | Hagen |
| 2009/0306717 A1 | 12/2009 | Kercher et al. |
| 2010/0004747 A1 | 1/2010 | Lin |
| 2010/0042218 A1 | 2/2010 | Nebosky et al. |
| 2010/0042221 A1* | 2/2010 | Boyd .................. A61F 2/28 623/17.16 |
| 2010/0076559 A1 | 3/2010 | Bagga et al. |
| 2010/0094426 A1 | 4/2010 | Grohowski, Jr. et al. |
| 2010/0137916 A1 | 6/2010 | Hynes et al. |
| 2010/0137990 A1 | 6/2010 | Apatsidis et al. |
| 2010/0185292 A1 | 7/2010 | Hochschuler et al. |
| 2010/0204737 A1 | 8/2010 | Bae et al. |
| 2010/0211119 A1 | 8/2010 | Refai et al. |
| 2010/0222750 A1 | 9/2010 | Cheng |
| 2010/0256773 A1 | 10/2010 | Thijs et al. |
| 2010/0262244 A1 | 10/2010 | Savage-Erickson et al. |
| 2010/0262245 A1 | 10/2010 | Alfaro et al. |
| 2010/0268343 A1 | 10/2010 | Dewey et al. |
| 2011/0004256 A1 | 1/2011 | Biedermann et al. |
| 2011/0004307 A1 | 1/2011 | Ahn et al. |
| 2011/0029081 A1 | 2/2011 | Malone |
| 2011/0046737 A1* | 2/2011 | Teisen ................ A61B 17/7097 606/86 A |
| 2011/0071635 A1 | 3/2011 | Zhang et al. |
| 2011/0092948 A1 | 4/2011 | Shachar et al. |
| 2011/0106159 A1 | 5/2011 | Nazeck |
| 2011/0160866 A1 | 6/2011 | Laurence et al. |
| 2011/0196494 A1 | 8/2011 | Yedlicka et al. |
| 2011/0196495 A1 | 8/2011 | Hunt |
| 2011/0224796 A1 | 9/2011 | Weiland et al. |
| 2011/0282392 A1 | 11/2011 | Murphy et al. |
| 2011/0282454 A1 | 11/2011 | Ullrich, Jr. et al. |
| 2011/0301709 A1 | 12/2011 | Kraus et al. |
| 2011/0313532 A1 | 12/2011 | Hunt |
| 2012/0029432 A1 | 2/2012 | Sweeney |
| 2012/0071933 A1 | 3/2012 | DeRidder |
| 2012/0078315 A1 | 3/2012 | Sweeney |
| 2012/0078373 A1 | 3/2012 | Gamache et al. |
| 2012/0123544 A1 | 5/2012 | Suh et al. |
| 2012/0172991 A1* | 7/2012 | Bertele ................ A61F 2/447 623/17.16 |
| 2012/0215315 A1 | 8/2012 | Hochschuler et al. |
| 2012/0253406 A1 | 10/2012 | Bae et al. |
| 2012/0265306 A1 | 10/2012 | Trieu |
| 2012/0277876 A1 | 11/2012 | Ullrich, Jr. et al. |
| 2012/0303127 A1 | 11/2012 | Ullrich, Jr. et al. |
| 2012/0312778 A1 | 12/2012 | Ullrich, Jr. et al. |
| 2012/0312779 A1 | 12/2012 | Patterson et al. |
| 2012/0330420 A1 | 12/2012 | Brodke et al. |
| 2013/0030529 A1 | 1/2013 | Hunt |
| 2013/0123925 A1 | 5/2013 | Patterson et al. |
| 2013/0123935 A1 | 5/2013 | Hunt et al. |
| 2013/0158672 A1 | 6/2013 | Hunt |
| 2013/0184822 A1 | 7/2013 | Kleiner |
| 2013/0218282 A1 | 8/2013 | Hunt |
| 2013/0226302 A1 | 8/2013 | Bae et al. |
| 2013/0274886 A1 | 10/2013 | Matsumoto et al. |
| 2013/0282122 A1 | 10/2013 | Ullrich, Jr. et al. |
| 2013/0292357 A1 | 11/2013 | Ullrich, Jr. et al. |
| 2013/0304218 A1 | 11/2013 | Ullrich, Jr. et al. |
| 2013/0306591 A1 | 11/2013 | Ullrich, Jr. et al. |
| 2013/0338777 A1 | 12/2013 | Bagga et al. |
| 2014/0025169 A1 | 1/2014 | Lechmann et al. |
| 2014/0031942 A1 | 1/2014 | Ullrich, Jr. et al. |
| 2014/0046449 A1 | 2/2014 | Ullrich, Jr. et al. |
| 2014/0052258 A1 | 2/2014 | Ball et al. |
| 2014/0114415 A1 | 4/2014 | Tyber |
| 2014/0114421 A1 | 4/2014 | Ullrich, Jr. et al. |
| 2014/0121776 A1 | 5/2014 | Hunt |
| 2014/0128924 A1 | 5/2014 | Perrow et al. |
| 2014/0200670 A1 | 7/2014 | Chin et al. |
| 2014/0277461 A1 | 9/2014 | Nebosky et al. |
| 2014/0277464 A1* | 9/2014 | Richter ................ A61F 2/4611 623/17.12 |
| 2014/0277482 A1 | 9/2014 | Gfeller et al. |
| 2014/0277491 A1 | 9/2014 | Fang et al. |
| 2014/0277511 A1 | 9/2014 | Ullrich, Jr. et al. |
| 2014/0277512 A1 | 9/2014 | Ullrich, Jr. et al. |
| 2014/0288649 A1 | 9/2014 | Hunt |
| 2014/0288650 A1 | 9/2014 | Hunt |
| 2014/0350682 A1 | 11/2014 | Bagga et al. |
| 2015/0012100 A1 | 1/2015 | Ullrich, Jr. et al. |
| 2015/0018956 A1 | 1/2015 | Steinmann et al. |
| 2015/0032220 A1 | 1/2015 | Tyber et al. |
| 2015/0045903 A1 | 2/2015 | Neal |
| 2015/0073422 A1 | 3/2015 | Chegini et al. |
| 2015/0157465 A1 | 6/2015 | Kirschman |
| 2015/0202047 A1 | 7/2015 | Patterson et al. |
| 2015/0202051 A1 | 7/2015 | Tanaka et al. |
| 2015/0230832 A1 | 8/2015 | Fraser et al. |
| 2016/0038301 A1 | 2/2016 | Wickham |
| 2016/0081818 A1 | 3/2016 | Waugh et al. |
| 2016/0199190 A1 | 7/2016 | Sharifi-Mehr et al. |

(56) References Cited

U.S. PATENT DOCUMENTS

| | | |
|---|---|---|
| 2017/0049491 A1 | 2/2017 | Ross et al. |
| 2017/0119537 A1 | 5/2017 | Tepper et al. |
| 2017/0182222 A1 | 6/2017 | Paddock et al. |
| 2017/0224388 A1 | 8/2017 | Walker et al. |
| 2017/0238974 A1 | 8/2017 | Konieczynski et al. |
| 2019/0008655 A1 | 1/2019 | Body |

FOREIGN PATENT DOCUMENTS

| | | |
|---|---|---|
| DE | 202013007361 U1 | 3/2014 |
| EP | 0179695 A1 | 4/1986 |
| EP | 0505634 A1 | 9/1992 |
| EP | 1327423 A1 | 7/2003 |
| EP | 1790298 A1 | 5/2007 |
| EP | 1872746 A2 | 1/2008 |
| FR | 2858546 A1 | 2/2005 |
| JP | 2002503135 A | 1/2002 |
| JP | 2004522516 A | 7/2004 |
| JP | 2011505978 A | 3/2011 |
| WO | 03005939 A2 | 1/2003 |
| WO | 03039400 A2 | 5/2003 |
| WO | 03053290 A1 | 7/2003 |
| WO | 2003092507 A2 | 11/2003 |
| WO | 2004071359 A1 | 8/2004 |
| WO | 2004080355 A1 | 9/2004 |
| WO | 2004108015 A2 | 12/2004 |
| WO | 2005051243 A2 | 6/2005 |
| WO | 2005071190 A2 | 8/2005 |
| WO | 2006033067 A3 | 3/2006 |
| WO | 2006051547 A2 | 5/2006 |
| WO | 2006074414 A2 | 7/2006 |
| WO | 2006086494 A2 | 8/2006 |
| WO | 2006121795 A2 | 11/2006 |
| WO | 2007028098 A2 | 3/2007 |
| WO | 2007087366 A2 | 8/2007 |
| WO | 2008014453 A2 | 1/2008 |
| WO | 2008021955 A2 | 2/2008 |
| WO | 2009099559 A2 | 8/2009 |
| WO | 2010021612 A1 | 2/2010 |
| WO | 2010028045 A1 | 3/2010 |
| WO | 2010052283 A1 | 5/2010 |
| WO | 2010121149 A2 | 10/2010 |
| WO | 2013133729 A1 | 9/2013 |
| WO | 2014018325 A1 | 1/2014 |

OTHER PUBLICATIONS

International Search Report and Writen Opinion, PCT/US2010/044988, dated Feb. 4, 2011.
International Search Report and Written Opinion for Application No. PCT/US2010/055259, dated Apr. 7, 2011.
European Search Report dated Sep. 26, 2012 for PCT/US2010022494.
Extended European Search Report for Application No. 14152779 dated Mar. 18, 2014.
Karageorgiou, V., and D. Kaplan. "Porosity of 3D Biomaterial Scaffolds and Osteogenesis", Biomaterials 26.27 (2005): 5474-491.
Harris, W. H. and M. Jasty (1985). "Bone ingrowth into porous coated canine acetabular replacements: the effect of pore size, apposition, and dislocation." Hip: 214-34.
Kujala, S. et al (2003): "Effect of porosity on the osteointegration and bone ingrowth of a weightbearing nickel-titanium bone graft substitute", Biomaterials, 24(25), Nov. 2003, pp. 4691-4697.
Callaghan, J. J. (1993). "The clinical results and basic science of total hip arthroplasty with porous-coated prostheses." J Bone Joint Surg Am 75(2): 299-310.
Wu, s et al (2013). Porous Ti6Al4V Cage Has Better Osseointegration and Less Micromotion Than a PEEK cage in Sheep Vertebral Fusion. Artificial organs 37(12).
Bobyn, J. D., G. J. Stackpool, S. A. Hacking, M. Tanzer, and J. J. Krygier. "Characteristics of Bone Ingrowth and Interface Mechanics of a New Porous Tantalum Biomaterial." The Journal of Bone and Joint Surgery81.5 (1999): 907-14.
Bobyn JD. Next generation porous metals forbiologic fixation. In: Glassman AH, Lachiewicz PF, Tanzer, M, eds. Orthopaedic Knowledge Update: Hip and Knee Reconstruction 4. Rosemont, IL: American Academy of Orthopaedic Surgeons; 2011:45-58.
Extended European Search Report for Application No. 15161713.1 dated Jun. 29, 2015.
Sharifi-Mehr et al., U.S. Appl. No. 14/994,697, filed Jan. 13, 2016.
Willis et al., U.S. Appl. No. 14/994,749, filed Jan. 13, 2016.
European Search Report for U.S. Appl. No. 16/170,075 dated Oct. 21, 2016.
Extended European Search Report for Application No. EP16171066 dated Dec. 14, 2016.
Extended European Search Report for Application No. EP16189379 dated Jun. 6, 2017.
Extended European Search Report for Application No. EP16202603 dated May 31, 2017.
Australian Examination Report for AU2017216532 dated Oct. 23, 2018.
Charles L. Bush, U.S. Appl. No. 62/653,877, filed Apr. 6, 2018, titled "Faceted Bone Plate".
Search Report for European Application No. 21158679.7 dated Sep. 24, 2021. 3 pgs.
Extended European Search Report for Application No. EP19213674.5, dated Mar. 11, 2020, pp. 1-4.

* cited by examiner

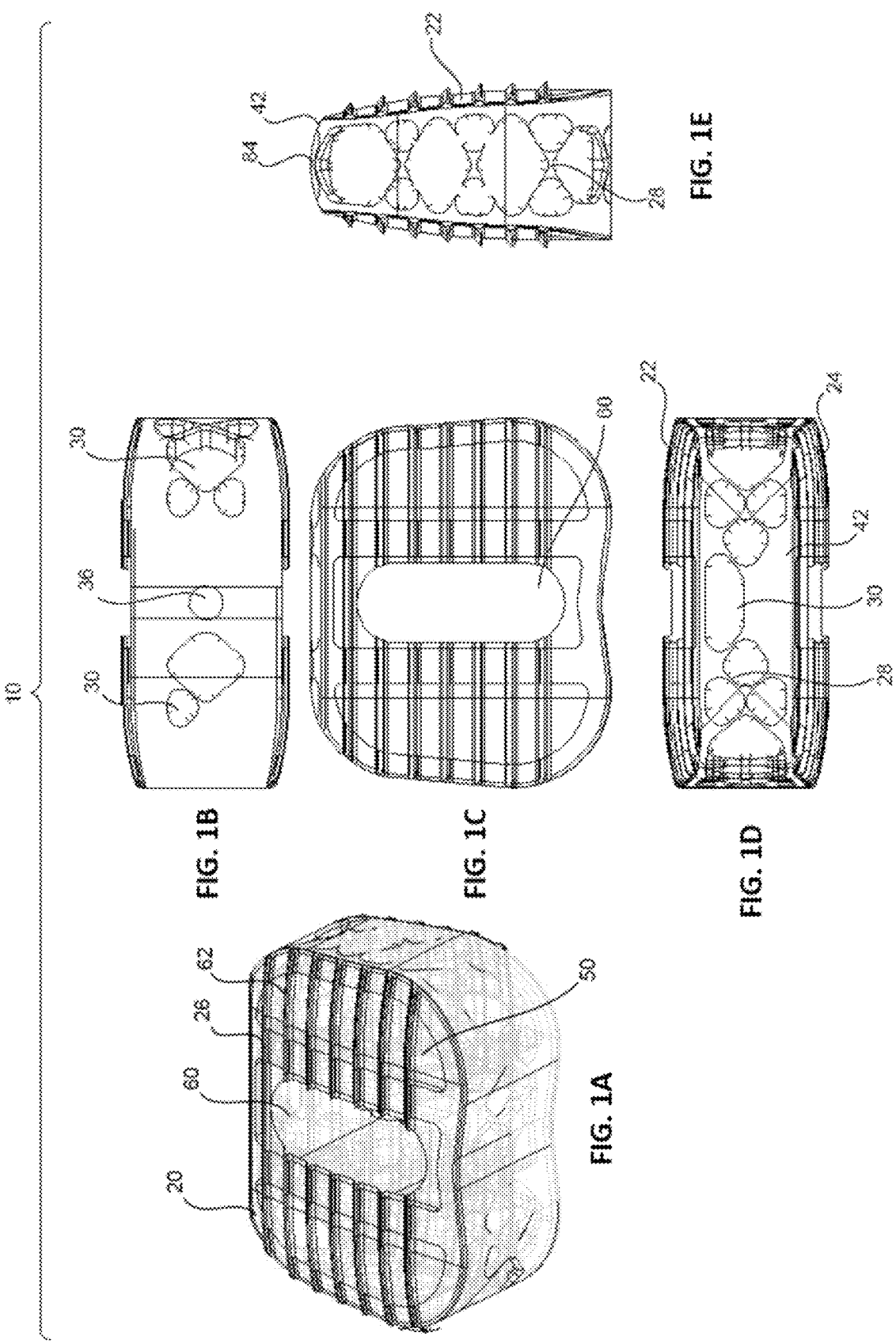

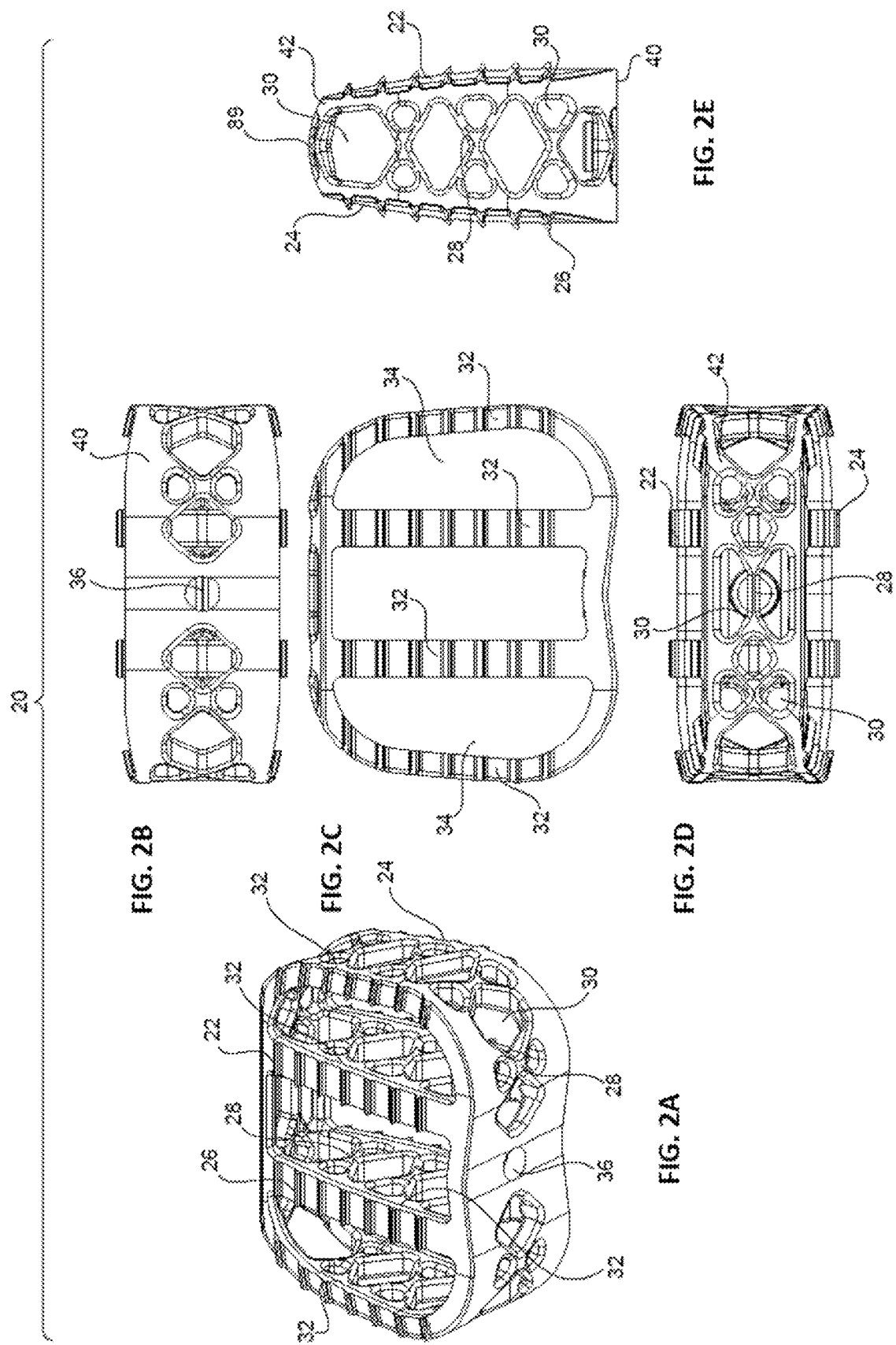

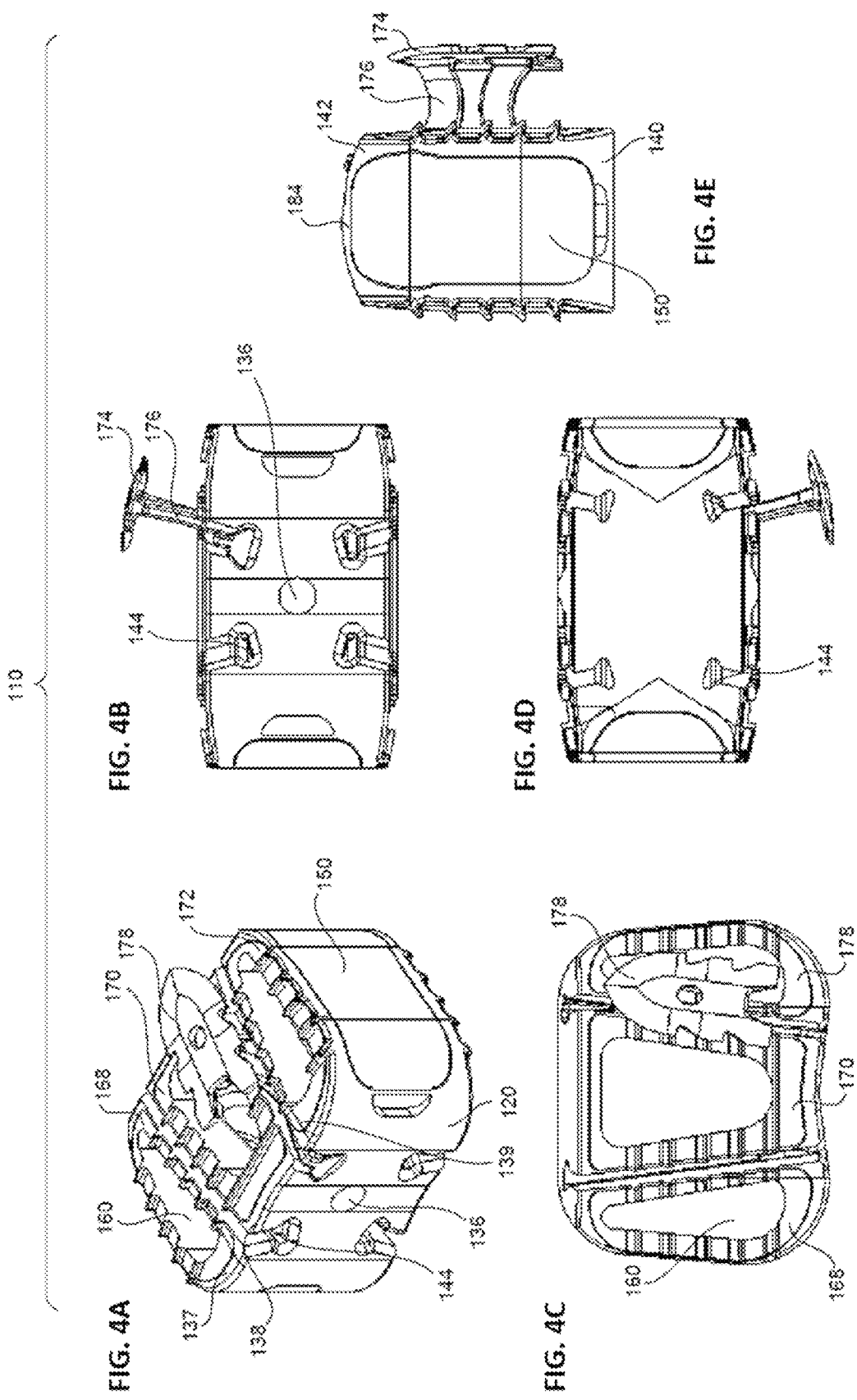

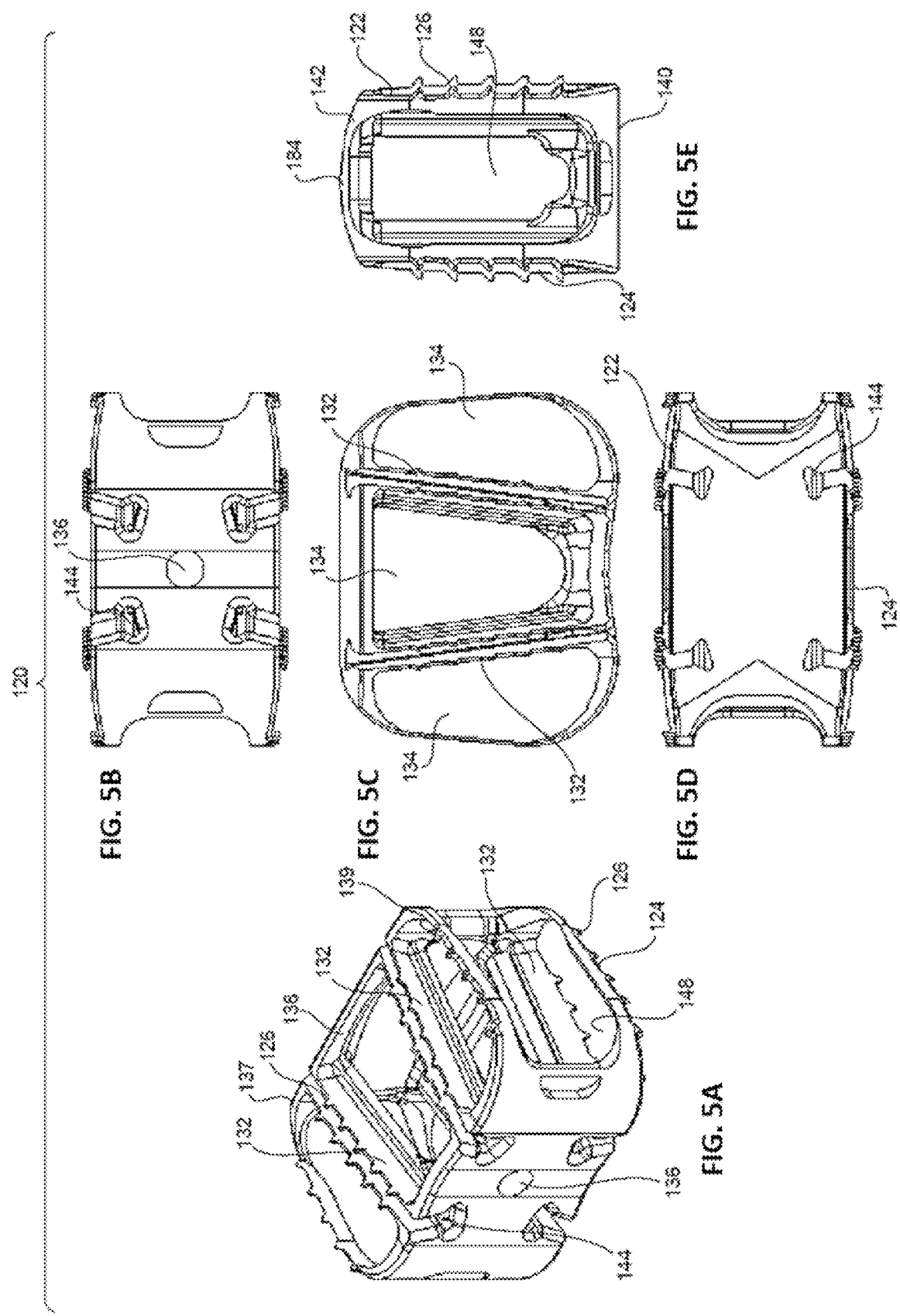

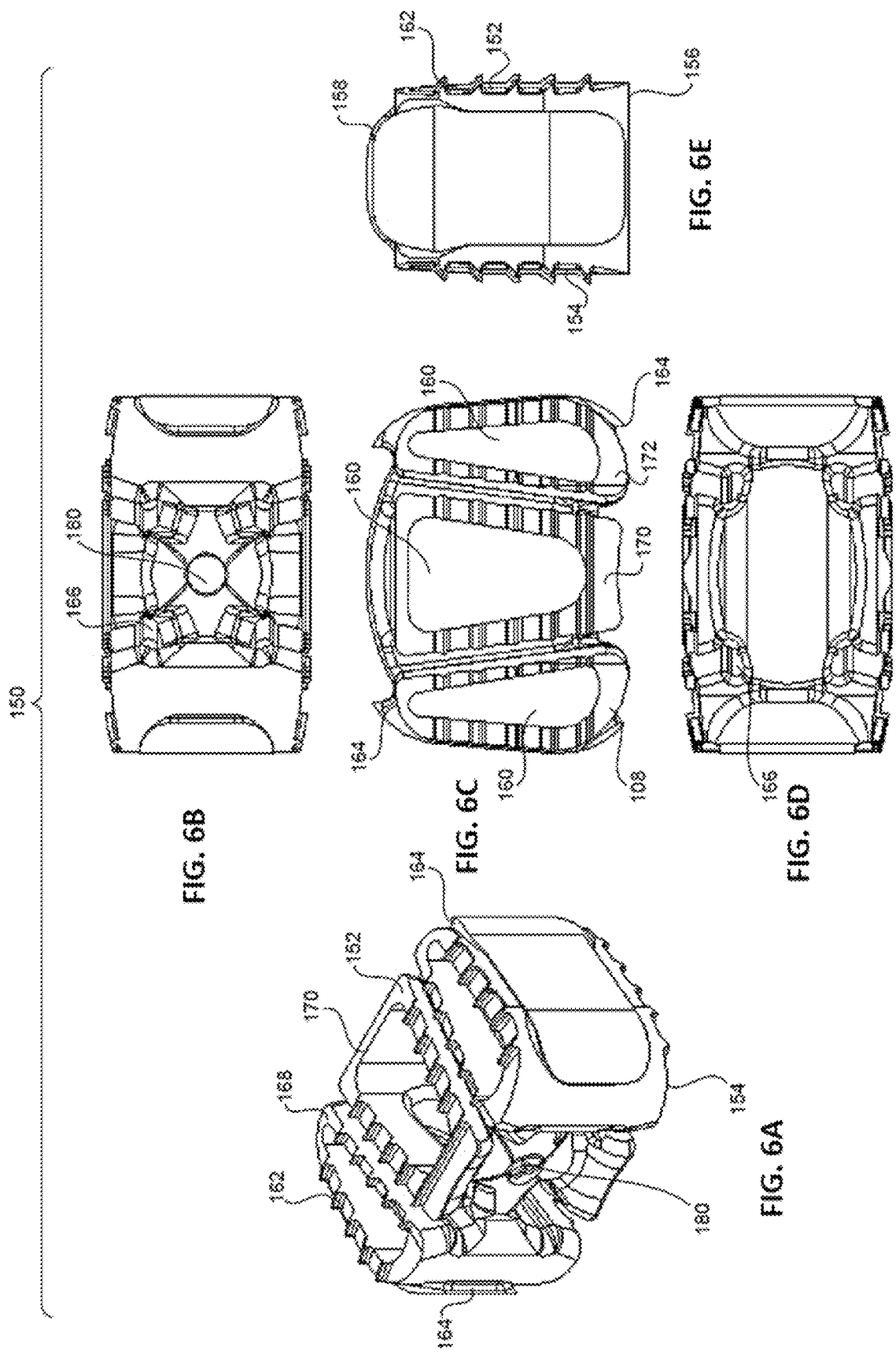

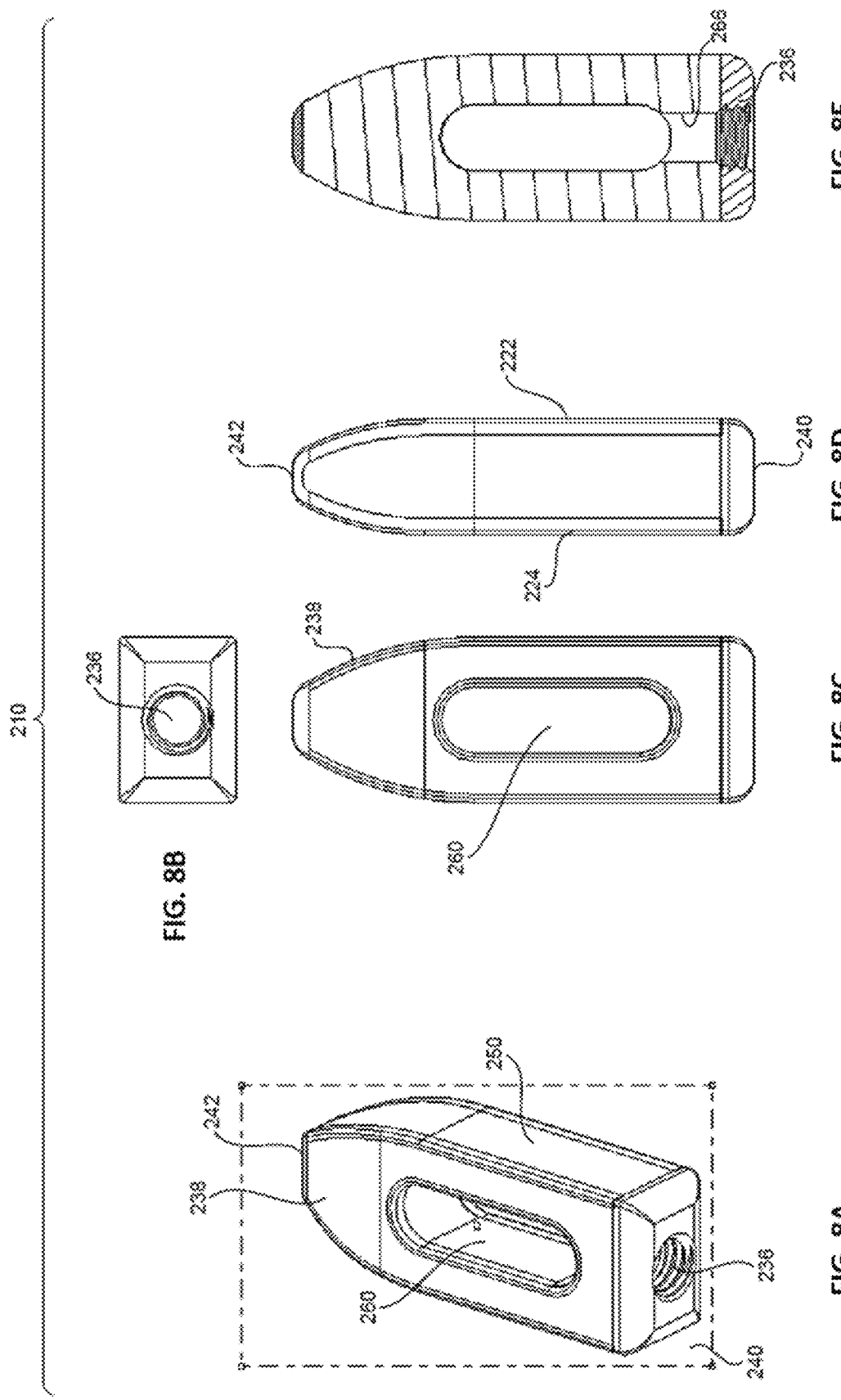

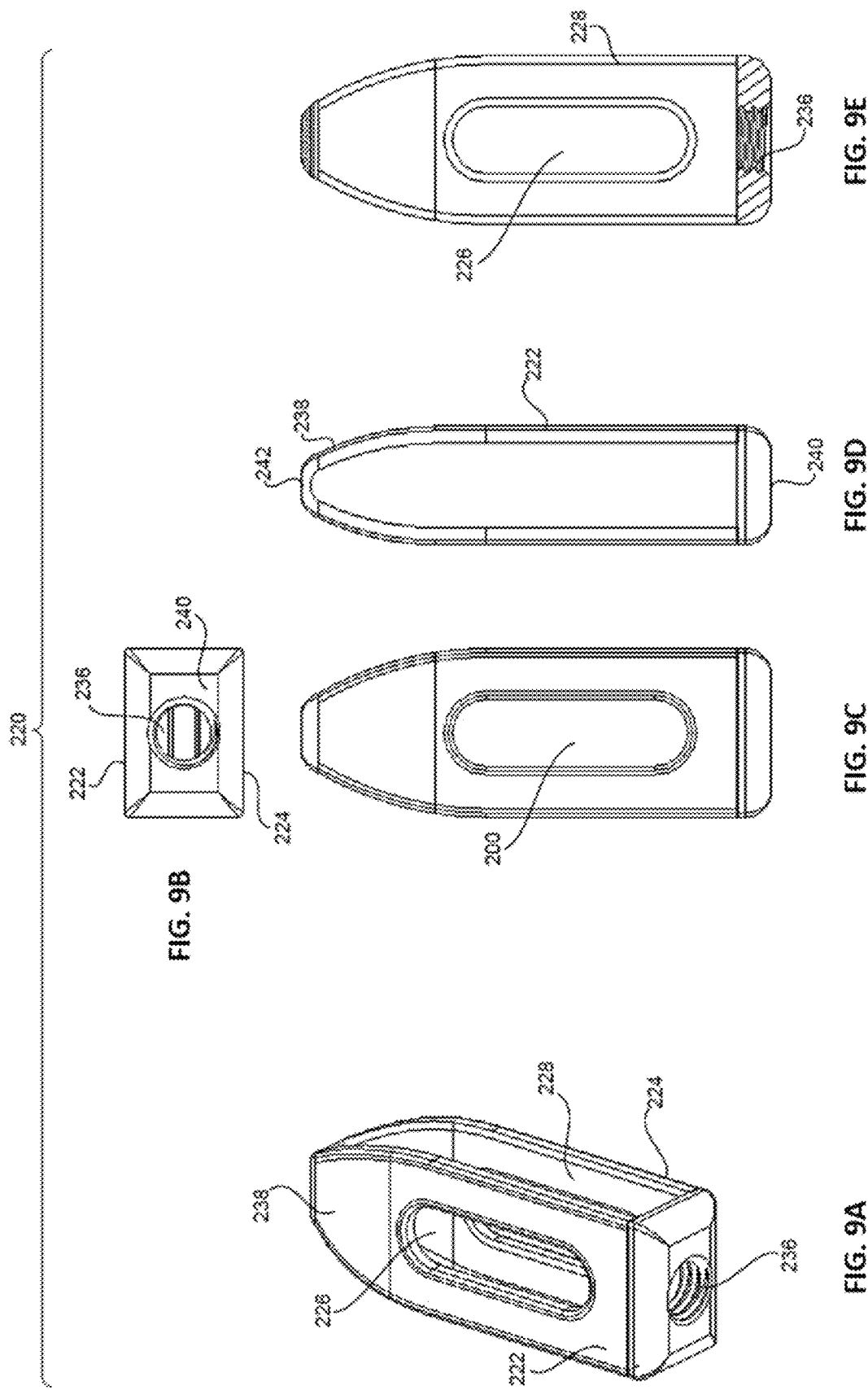

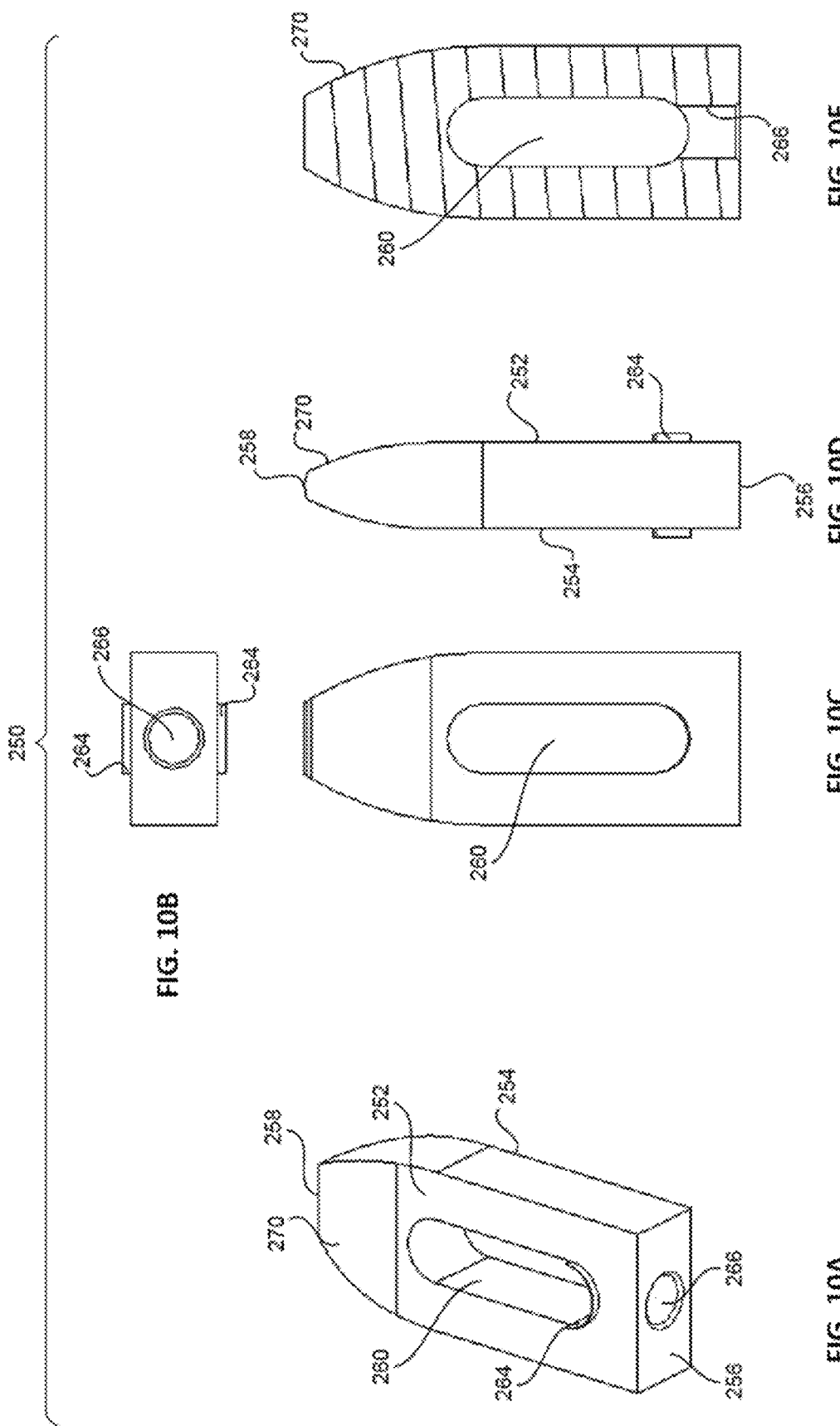

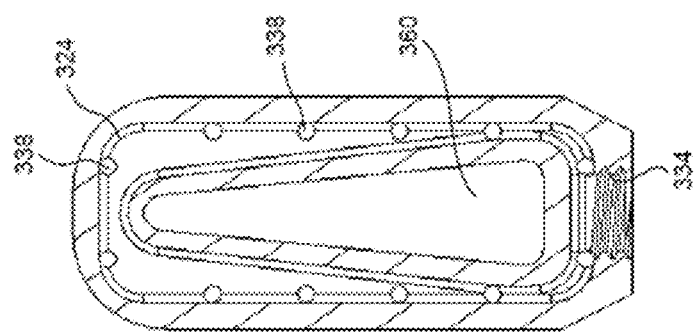
FIG. 11E
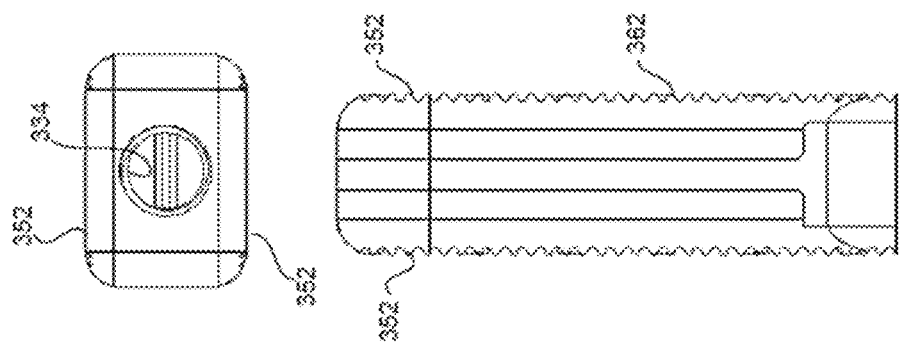
FIG. 11B
FIG. 11D
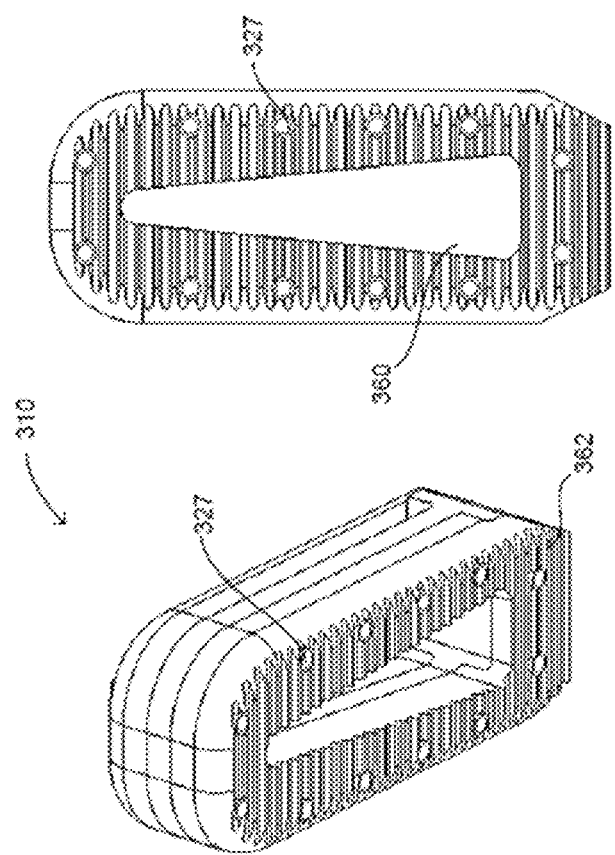
FIG. 11C
FIG. 11A

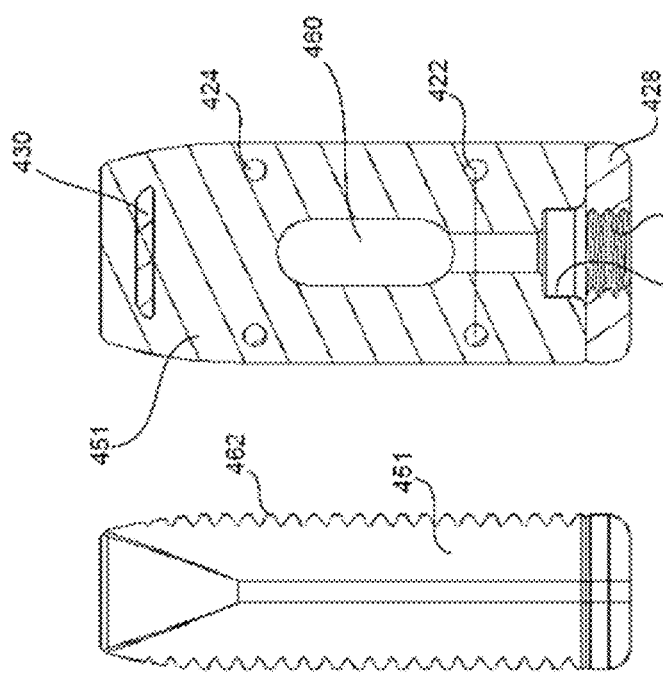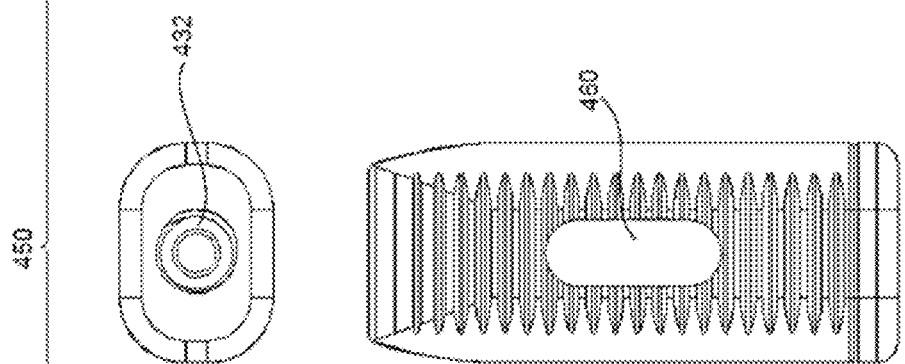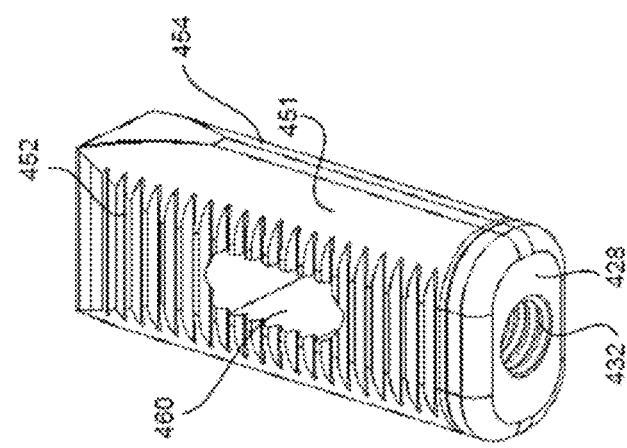

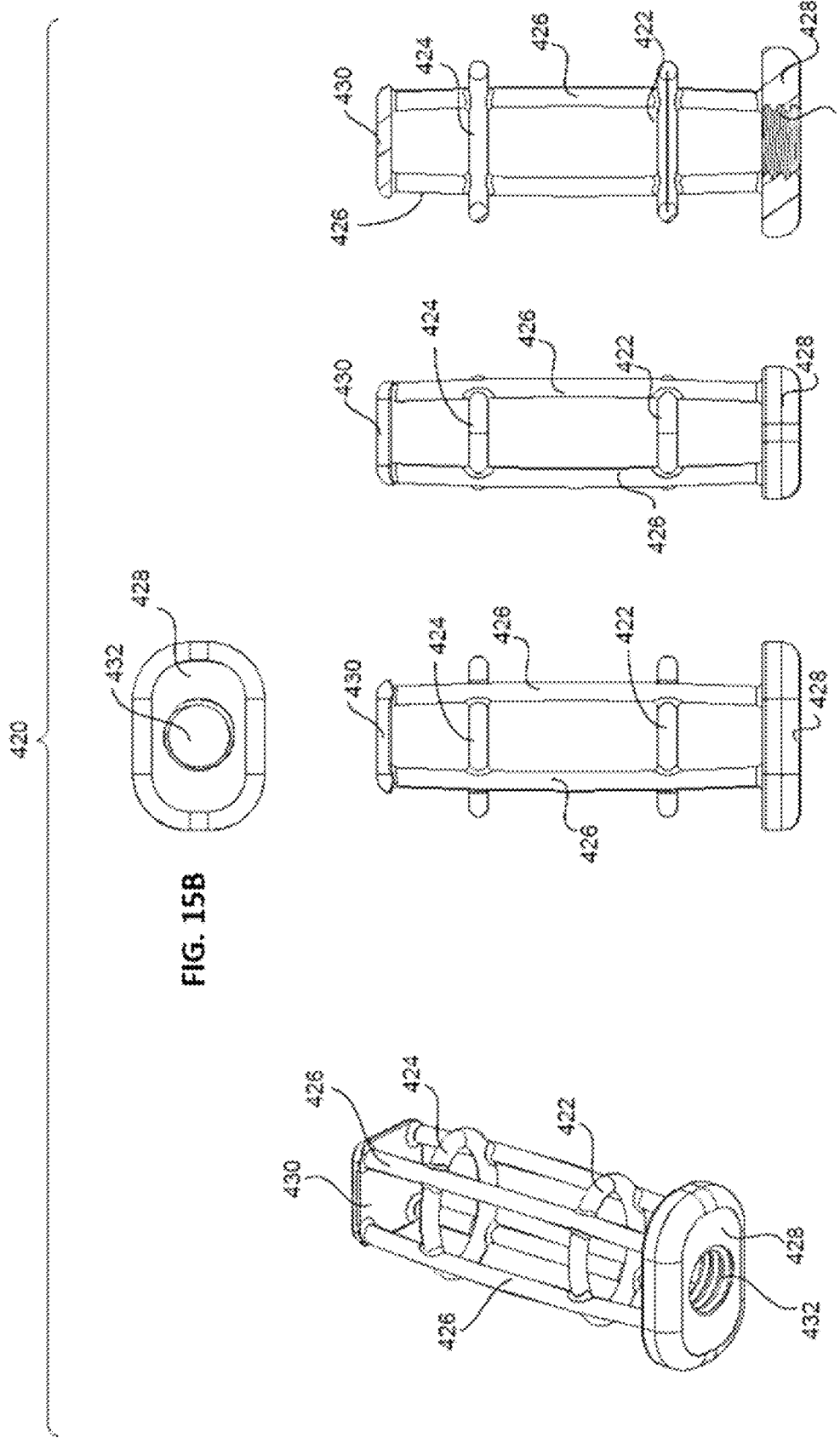

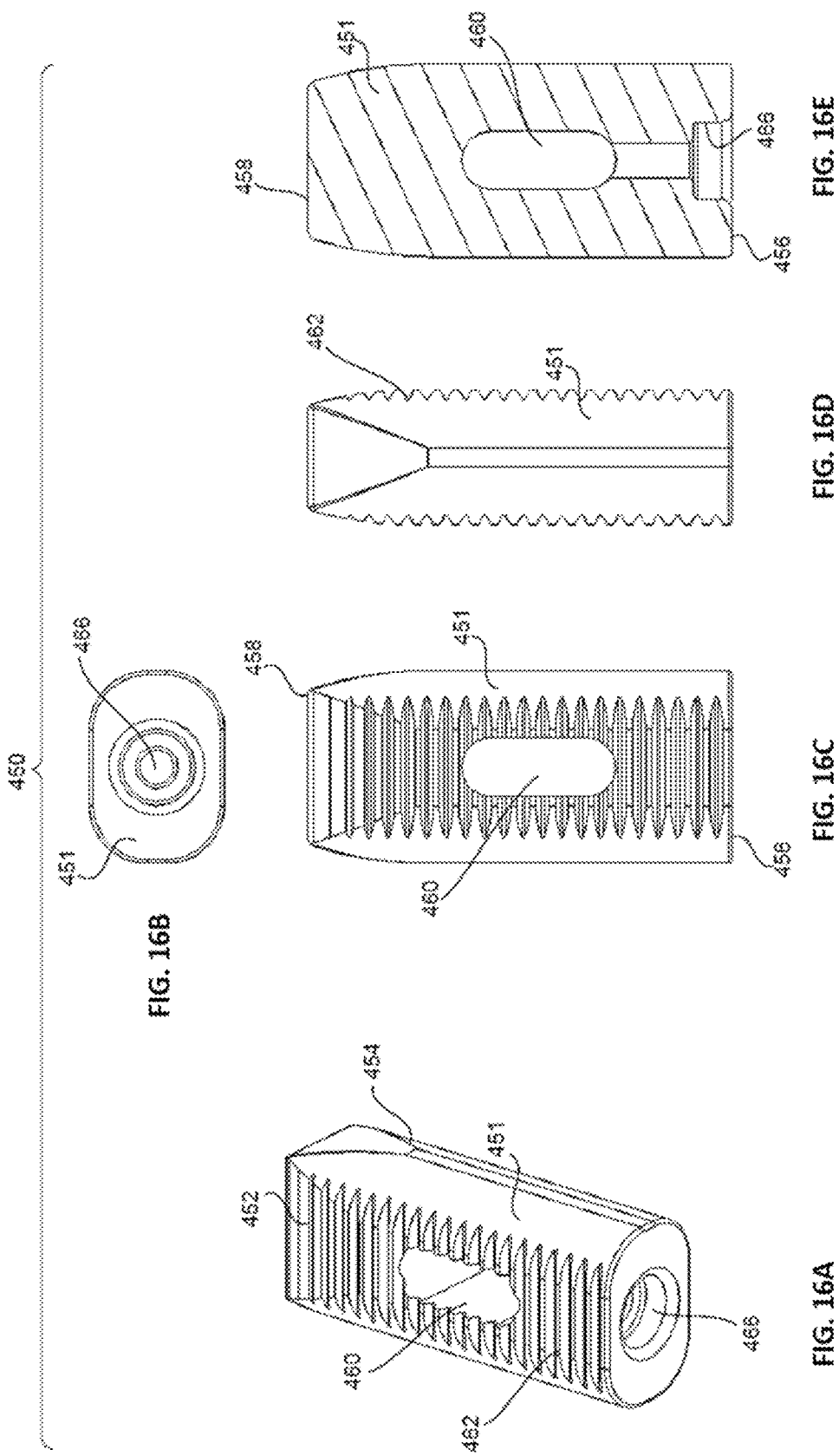

PARTIALLY RESORBABLE IMPLANTS AND METHODS

CROSS-REFERENCE TO RELATED APPLICATIONS

This application is a continuation of U.S. application Ser. No. 15/158,202, filed on May 18, 2016, which claims the benefit of U.S. Provisional Application No. 62/163,146 filed on May 18, 2015, the disclosures of which are incorporated by reference herein.

BACKGROUND OF THE INVENTION

The present invention relates to spinal surgery, namely the fusion of adjacent intervertebral bodies or the replacement of a vertebral body.

Back pain can be caused by many different maladies, not the least of which are problems that directly impact the intervertebral discs of the spine. Typical disc issues include, inter alia, degeneration, bulging, herniation, thinning, abnormal movement, spondylosis, spinal stenosis, disc herniation, retrolisthesis, and discogenic back pain. One method of treatment of such disc problems that is widely utilized in the field of spinal surgery is a spinal fusion procedure, whereby an affected disc is removed, and the adjacent vertebral bodies are fused together through the use of interbody spacers, implants, or the like. In some instances, it may also be necessary to remove and replace an entire vertebral body. This is often accomplished through the use of a larger implant that acts to fuse together the vertebral bodies adjacent the removed vertebral body.

In replacing a diseased intervertebral disc(s) and affecting fusion, it may also be necessary to ensure that proper spacing is maintained between the vertebral bodies. It is also the case that an implant must be structured to effectively support and bear the post-surgical loads inherent in movement of the adjacent vertebral bodies of the spine after implantation. At the same time, proper and effective fusion of the vertebral bodies is of concern. Thus, implants exist in which resorbable materials are used to promote fusion, but in many cases these implants are not structurally sound or are susceptible to failure in one way or another. As an example, allograft spacers constitute a resorbable material, but such spacers are often brittle during implantation and can fracture. Other drawbacks to existing resorbable implants also exist.

Therefore, there exists a need for an improved spinal implant.

BRIEF SUMMARY OF THE INVENTION

A first aspect of the invention includes an implant sized and adapted for insertion into an intervertebral space between adjacent vertebral bodies. The implant comprises a non-resorbable, structural framework having top and bottom bone-contacting surfaces and a plurality of struts defining geometric openings between the top and bottom surfaces, the struts providing structural support for the framework, wherein the framework includes a plurality of support columns extending between proximal and distal ends of the framework, the plurality of support columns being spaced apart from each other to define vertical openings in the framework. The implant also includes a resorbable material component within and/or around the framework for resorption and formation of new bone to fuse the vertebral bodies together. In certain embodiments of this first aspect, the resorbable material component is a structural component that includes top and bottom bone-contacting surfaces configured to support post-surgical loads experienced after implantation of the implant.

A second aspect of the invention includes an implant sized and adapted for insertion into an intervertebral space between adjacent vertebral bodies. The implant comprises a non-resorbable, non-structural framework having top and bottom bone-contacting surfaces formed of a porous material, and a resorbable, structural component positioned between the top and bottom surfaces of the framework to provide structural support for the top and bottom surfaces and the implant. In an embodiment of this second aspect, the top and bottom surfaces of the framework are two millimeters (2 mm) or less in thickness.

A third aspect of the invention includes an implant sized and adapted for insertion into an intervertebral space between adjacent vertebral bodies. The implant comprises a non-structural, non-resorbable framework having a main body and a fluid conduit within the main body, the main body having an injection port in fluid communication with the fluid conduit. The implant also includes a resorbable, structural component having top and bottom bone-contacting surfaces and an opening in at least one of the top and bottom surfaces, the opening being in fluid communication with the fluid conduit. In an embodiment of this third aspect, a fluid conduit projects outward from the main body and is fluidly connected with the fluid conduit in the main body, wherein the outwardly-projecting fluid conduit defines the opening in the at least one of the top and bottom surfaces of the resorbable, structural component.

A fourth aspect of the invention includes an implant sized and adapted for insertion into an intervertebral space between adjacent vertebral bodies. The implant comprises a non-structural, non-resorbable framework having a series of ring members connected together by way of a plurality of struts, and a resorbable, structural component embedded with and/or around the framework for encouraging resorption of the implant and fusion of the vertebral bodies. In an embodiment of this fourth aspect, the ring members are arranged transverse to a longitudinal axis of the framework, and the struts extend along the longitudinal axis and connect the ring members.

A fifth aspect of the invention includes a method of reducing subsidence of an implant into bone. The method comprises providing an implant having a non-resorbable structural framework and a resorbable structural component positioned within and/or around the framework. The framework is implanted between first and second adjacent vertebral bodies so that top and bottom surfaces of the framework contact vertebral endplates of the first and second vertebral bodies, and the resorbable component is likewise implanted between the first and second adjacent vertebral bodies so that top and bottom surfaces of the resorbable component contact the vertebral endplates. Once implanted, the top and bottom surfaces of the resorbable component contact the vertebral endplates over a contact surface area sufficient to reduce peak stresses between the framework and the vertebral bodies by an amount effective to eliminate or reduce subsidence of the framework into the vertebral bodies. In an embodiment of this fifth aspect, in the absence of the resorbable component, peak stresses between the framework and the vertebral bodies is above a stress required for the vertebral endplates to fail, for example above 160 MPa.

A sixth aspect of the invention includes an implant sized and adapted for insertion into an intervertebral space between adjacent vertebral bodies. The implant comprises a non-resorbable, structural framework having top and bottom bone-contacting surfaces and a plurality of struts defining geometric openings between the top and bottom surfaces, the struts providing structural support for the framework. The implant also includes a resorbable material component within and/or around the framework for resorption and formation of new bone to fuse the vertebral bodies together, wherein the resorbable material has top and bottom bone-contacting surfaces, and the top and bottom surfaces of the resorbable component are arranged to contact the vertebral endplates over a contact surface area sufficient to reduce peak stresses between the framework and the vertebral bodies by an amount effective to reduce or eliminate subsidence of the framework into the vertebral bodies. In an embodiment, the contact surface area is between about 30-70% of an overall contact surface area of the implant in contact with the vertebral endplates. In another embodiment, in the absence of the resorbable component, peak stresses between the framework and the vertebral bodies is above a stress required for the vertebral endplates to fail.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

A more complete appreciation of the subject matter of the present invention and of the various advantages thereof can be realized by reference to the following detailed description in which reference is made to the accompanying drawings in which:

FIGS. 1A-E are perspective (1A), proximal (1B), top (1C), distal (1D), and side (1E) assembled views of an implant having a non-resorbable, structural framework and a resorbable component positioned within and/or around the framework, in accordance with an embodiment of the present invention.

FIGS. 2A-E are perspective (2A), proximal (2B), top (2C), distal (2D), and side (2E) views of the non-resorbable, structural framework of the implant of FIGS. 1A-E.

FIGS. 4A-E are perspective (4A), proximal (4B), top (4C), distal (4D), and side (4E) assembled views of an implant having a non-resorbable, structural framework and a resorbable component positioned within and/or around the framework, in accordance with another embodiment of the present invention.

FIGS. 5A-E are perspective (5A), proximal (5B), top (5C), distal (5D), and side (5E) views of the non-resorbable, structural framework of the implant of FIGS. 4A-E.

FIGS. 6A-E are perspective (6A), proximal (6B), top (6C), distal (6D), and side (6E) views of the resorbable component of the implant of FIGS. 4A-E.

FIGS. 8A-E are perspective (8A), proximal (8B), top (8C), side (8D), and cross-sectional (8E) assembled views of an implant having a porous, non-resorbable, non-structural framework and a resorbable, structural component positioned within and/or around the framework, in accordance with yet another embodiment of the present invention.

FIGS. 9A-E are perspective (9A), proximal (9B), top (9C), side (9D), and cross-sectional (9E) views of the framework of the implant of FIGS. 8A-E.

FIGS. 10A-E are perspective (10A), proximal (10B), top (10C), side (10D), and cross-sectional (10E) views of the resorbable, structural component of the implant of FIGS. 8A-E.

FIGS. 11A-E are perspective (11A), proximal (11B), top (11C), side (11D), and cross-sectional (11E) assembled views of an implant having a non-resorbable framework with fluid channels and a resorbable, structural component positioned within and/or around the framework, in accordance with yet another embodiment of the present invention.

FIGS. 14A-E are perspective (14A), proximal (14B), top (14C), side (14D), and cross-sectional (14E) assembled views of an implant having a non-structural, non-resorbable framework and a resorbable, structural component positioned within and/or around the framework, in accordance with yet another embodiment of the present invention.

FIGS. 15A-E are perspective (15A), proximal (15B), top (15C), side (15D), and cross-sectional (15E) views of the non-structural, non-resorbable framework of the implant of FIGS. 14A-E.

FIGS. 16A-E are perspective (16A), proximal (16B), top (16C), side (16D), and cross-sectional (16E) views of the resorbable, structural component of the implant of FIGS. 11A-E.

DETAILED DESCRIPTION

Figure 3E:
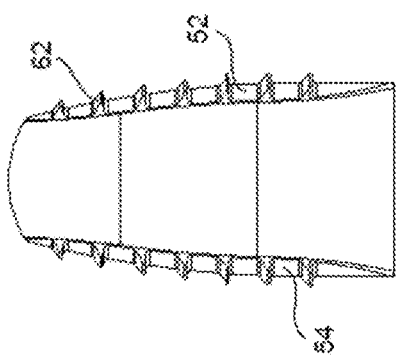
FIGS. 3A-E are perspective (3A), proximal (3B), top (3C), distal (3D), and side (3E) views of the resorbable component of the implant of FIGS. 1A-E.
Figures 3B, 3C, 3D:
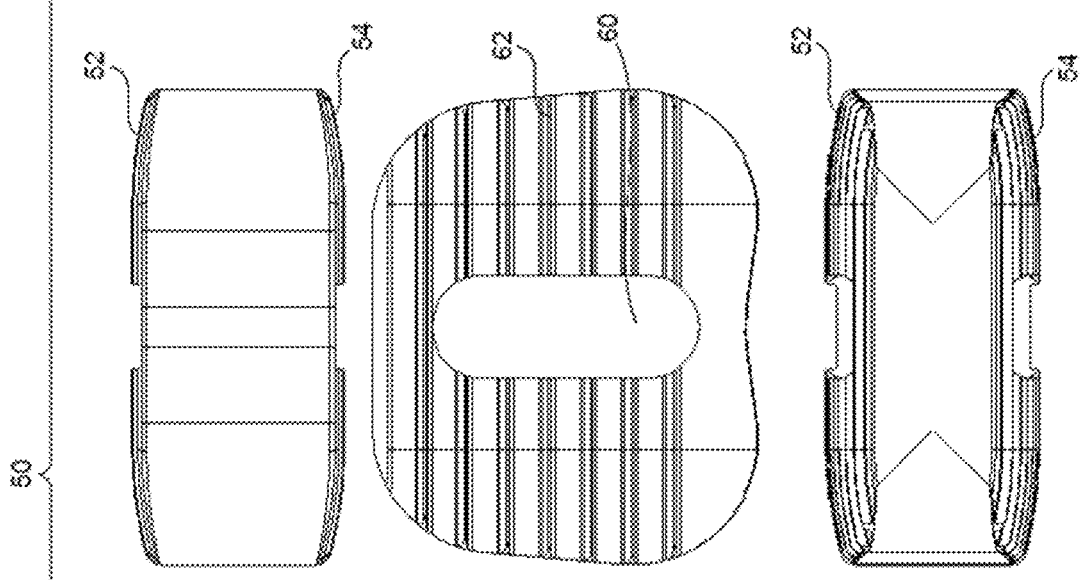
Figure 3A:
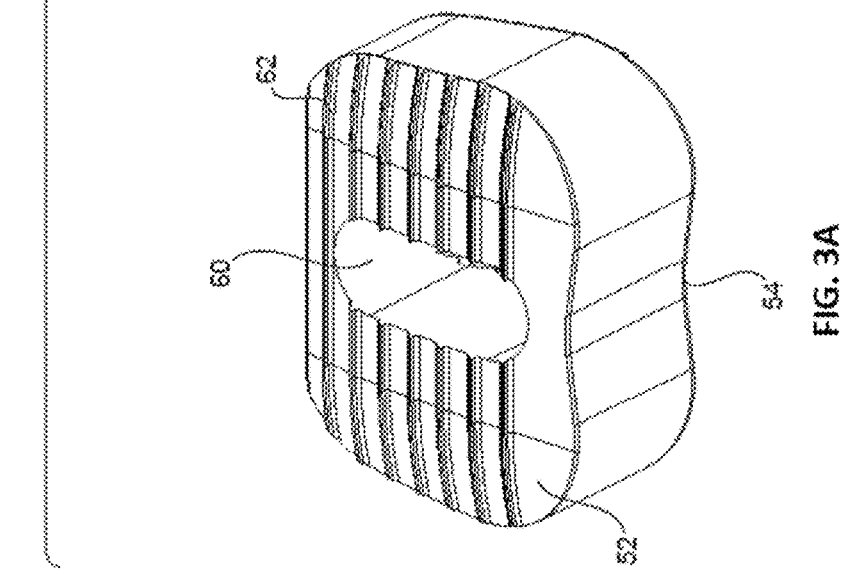

In describing the preferred embodiments of the invention illustrated and to be described with respect to the drawings, specific terminology will be used for the sake of clarity. However, the invention is not intended to be limited to any specific terms used herein, and it is to be understood that each specific term includes all technical equivalents, which operate in a similar manner to accomplish a similar purpose.

As used herein, the term "structural" means the ability to bear the post-operative service load without the need for a second material. The term "structural" is not restricted to the ability to bear the entire post-operative service load, and may include bearing some (e.g., a therapeutically effective amount) or a majority of the post-operative service load.

The present invention includes a variety of implants that have a non-resorbable framework or skeleton, in certain cases providing structural support and in other cases being non-structural, in combination with a resorbable component or material that is embedded within and/or around the framework. The resorbable component provides structural support in some cases or is non-structural in others. The particular combination of a non-resorbable framework along with a resorbable component or material, as disclosed herein, allows an implant to adequately support adjacent vertebral bodies when implanted during a fusion process while also encouraging positive bone formation and resorption of the implant.

Referring to FIGS. 1A-E, an implant 10 is shown that has a non-resorbable structural framework 20 and a resorbable component/material 50 embedded within framework 20. Framework 20 provides structural support for implant 10, while resorbable material 50 encourages or allows for bone formation and fusion for adjacent vertebral bodies contacting implant 10.

Framework 20 is shown in detail in FIGS. 2A-E. Framework 20 includes top and bottom bone-contacting surfaces 22, 24, proximal and distal ends 40, 42, and teeth 26 formed on top and bottom surfaces 22, 24. In some cases, framework 20 is formed through an additive manufacturing process, such as selective laser melting (SLM), selective laser sintering (SLS), 3D printing, or any other additive process. Through the additive process (or by using another manufacturing method), framework 20 is created to include a network of struts 28 that define a variety of differently-shaped geometric openings 30. Indeed, the body of framework 20 may be successively composed layer-by-layer through an additive process, as detailed above, so that struts 28 are formed to define the different geometric openings 30 of framework 20. In an embodiment, geometric openings 30 are present along the sides of framework 20, at proximal and distal ends 40, 42, and along a series of support columns 32 of framework 20. Thus, geometric openings 30 can provide access to and throughout an interior of framework 20 so that bone growth can occur into framework 20, as described in more detail below.

Support columns 32 of framework 20 each include various struts 28 defining geometric openings 30, which act to provide structural support for framework 20. In an embodiment, framework 20 is designed to bear a substantial portion (e.g., fifty percent (50%) or more) of the anticipated post-surgical load for implant 10. Support columns 32 also each include portions of top and bottom bone-contacting surfaces 22, 24 of framework 20, which have teeth 26. Struts 28 support such portions of top and bottom bone-contacting surfaces 22, 24. Support columns 32 also define vertical openings 34 in framework 32, which may provide areas for resorbable material 50 to extend between.

As shown in FIGS. 2A-B and 2E, respectively, framework 20 also includes an opening 36 (optionally threaded) at its proximal end 40 for attachment with an implantation tool (not shown), as well as a bulleted nose 84 at its distal end 42 to ease implantation of implant 10 into a disc space between adjacent vertebral bodies.

In an exemplary embodiment, framework 20 is composed of titanium or titanium alloy (porous or solid), tantalum, stainless steel, polyetheretherketone (PEEK), polyetherketoneketone (PEKK), or a material developed by the Applicant, which is referred to as Cortoss®. Combinations of the foregoing materials may also be used. Non-resorbable framework 20 can also incorporate osteoconductive materials, resorbable coatings, or resorbable materials within voids or pores of the non-resorbable material to make framework 20 an active participant in the fusion process. As an example, framework 20 may be constructed of solid and porous portions, as described in Applicant's U.S. Patent Application Ser. No. 62/103,276, filed Jan. 14, 2015, now U.S. patent application Ser. No. 14/994,749, which are hereby incorporated by reference herein. The '276 application was attached as Exhibit A to the '146 Provisional. As set forth therein, in particular embodiments, the teeth of certain implants can be formed from porous and solid structures. Such teeth could be incorporated into framework 20, or used with any other implant described in more detail below. Additionally, the '276 application describes other implant structures with porous and solid features, and it is contemplated that such technology may be used with framework 20, or any other framework or implant discussed more fully below.

In an embodiment, top and bottom surfaces 22, 24 of framework 20 are also tapered towards one another by a degree sufficient to accommodate the natural lordosis that may exist between the adjacent vertebral bodies. Such lordosis exists, for example, between adjacent vertebral bodies in the lumbar spine. Other embodiments, however, may include parallel top and bottom surfaces 22, 24.

Resorbable component/material 50 is shown in FIGS. 3A-E. In an embodiment, resorbable material 50 comprises a flowable/curable material that is embedded within and/or around framework 20. Resorbable material 50 may also provide structural support for implant 10 by defining top and bottom surfaces 52, 54 that are arranged to contact adjacent vertebral bodies, in addition to top and bottom surfaces 22, 24 of framework 20, and support the vertebral bodies once implant 10 is implanted. Indeed, as shown in FIGS. 1A-E, once material 50 is embedded within framework 20, it fills in the space between certain support columns 32 and provides top and bottom surfaces 52, 54 that are arranged to contact adjacent vertebral bodies. Further, top and bottom surfaces 52, 54 include teeth 62 for digging into the vertebral bodies. In an embodiment, top and bottom surfaces 52, 54 are also tapered towards one another by a degree sufficient to accommodate the natural lordosis that may exist between the adjacent vertebral bodies, but can also be arranged parallel.

Resorbable material/component 50 also includes a single vertical opening 60 that, when combined with framework 20, provides a vertical opening 60 in implant 10. Vertical opening 60 may receive, for example, a bone graft material to further enhance the resorptive characteristics of implant 10 and promote fusion.

In an exemplary embodiment, resorbable material 50 is composed of bioactive glass, bone, polylactides, collagen, magnesium alloy, or a Cross-Linked Microstructure (CLM) bioglass material developed by Bio2 Technologies, Inc. as described, for instance, in Bio2 Technologies' U.S. Pat. No. 8,673,016, which is hereby incorporated by reference herein. Combinations of the foregoing materials may also be used. Resorbable material 50 may include one of the materials above in a collagen or other polymeric carrier to facilitate molding into framework 20. A template manufacturing process may also be used in which calcium phosphate, sol-gel derived bioactive glass, or another ceramic is produced on a porous template which occupies the openings within framework 20, and is then sacrificed by heat treatment so that only the ceramic is left behind. It may also be desirable to fill framework 20 with a powder, particulate, or fiber form of resorbable material 50 in a mold and then further process by heat, chemical cross-linking or other means to bond or sinter the powder, particulate, or fibers into a solid or porous final state which fills framework 20.

In one case, resorbable material 50 may comprise a majority of the overall material volume of implant 10, for example fifty percent (50%) or more of the overall volume. Resorbable material 50 may be embedded within struts 28. In addition, although resorbable material 50 is described above as providing structural support for implant 10, in an alternate embodiment resorbable material is non-structural depending upon the intended implementation for implant 10. For example, a non-structural resorbable component 50 may be useful for applications in which loading is expected to be predictable or additional resistance to subsidence into bone is not required. A structural resorbable component 50 may be required to add surface area to reduce local contact pressure where implant 10 contacts bone for configurations in which structural framework 20 is not adequate to prevent subsidence or other failure of the bone, despite framework 20 having the necessary strength to withstand the service load. In either case, the combination of resorbable component 50 and framework 20 results in a greater fusion mass than what a traditional PEEK or titanium cage would allow, as a majority of implant 10's volume becomes resorbed and replaced by bone.

In another embodiment, non-resorbable framework 20 may be composed of a radiopaque material, and the particular arrangement of framework 20 may optimize visualization of the resulting fusion mass within or around the implant. For instance, as shown in the side view of FIG. 1E, framework 20, in particular struts 28 thereof, define geometric openings 30 of roughly a diamond shape within an otherwise radiopaque structure, which allows for viewing the resulting fusion mass using standard imaging techniques from a lateral perspective. Moreover, the minimal amount of radiopaque material in this area, as well as the extent of geometric openings 30, provide direct visualization of resorbable component 50 under visualization. Generally, with prior art devices, the fusion mass would be occluded from a lateral perspective due to the presence of a radiopaque structure(s) blocking visualization of the mass.

Figure 7:
FIG. 7 is a Finite Element Analysis of the structural framework of the implant of FIGS. 1A-E.
Figure 12E:
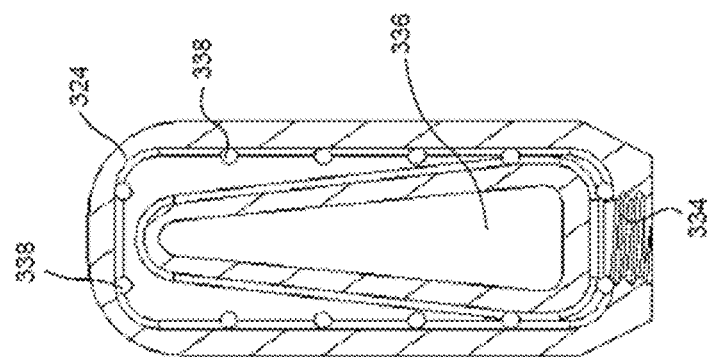
FIGS. 12A-E are perspective (12A), proximal (12B), top (12C), side (12D), and cross-sectional (12E) views of the non-resorbable framework of the implant of FIGS. 11A-E.
Figure 12D:
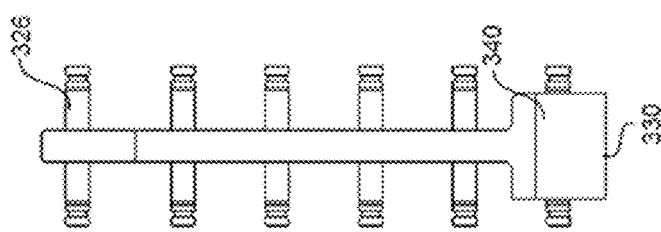
Figure 12B:
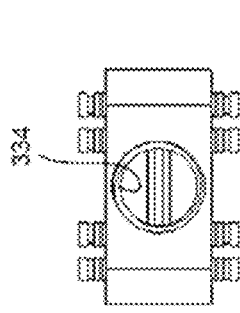
Figure 12C:
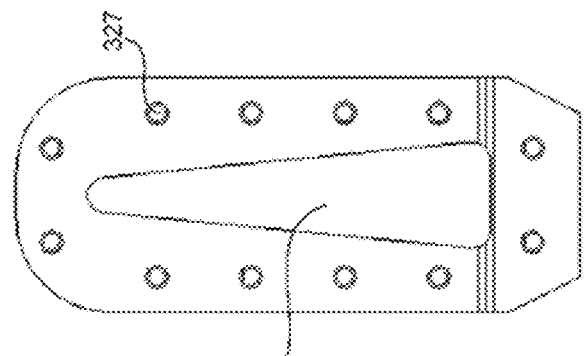
Figure 12A:
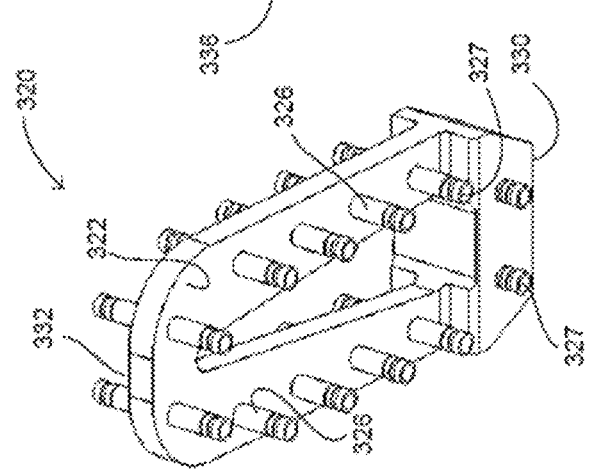
Figure 13E:
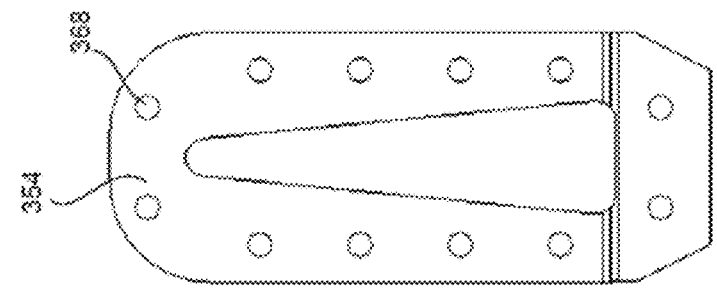
FIGS. 13A-E are perspective (13A), proximal (13B), top (13C), side (13D), and cross-sectional (13E) views of the resorbable, structural component of the implant of FIGS. 11A-E.
Figure 13D:
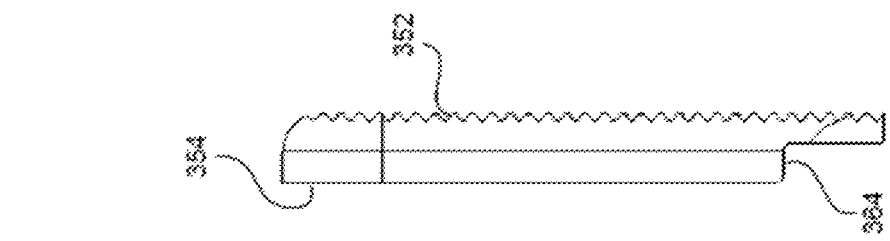
Figures 13B, 13C:
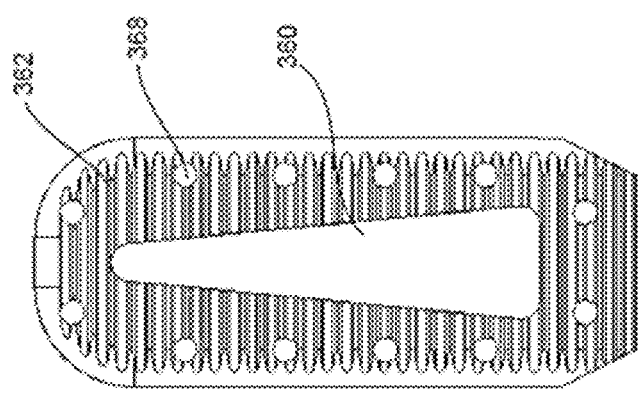
Figure 13A:
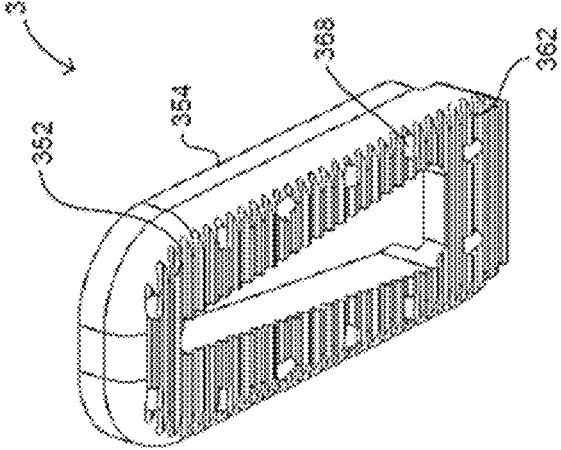

FIG. 7 shows a Finite Element Analysis of framework 20 demonstrating the post-operative loads that framework 20 can withstand. The Finite Element Analysis illustrates a load of 10,000 Newtons being applied to framework 20, and the subsequent stresses seen in framework 20. As illustrated, framework 20 can withstand the 10,000 Newton load (or greater) without yielding. A load of 10,000 N was selected as it is representative of a typical dynamic service load.

Figure 25:
FIG. 25 is a Finite Element analysis of a certain load being applied only to the framework of FIGS. 2A-E, without the resorbable component of FIGS. 3A-E.

FIG. 25 shows another Finite Element Analysis of framework 20 (without resorbable component 50) in which the scale of the Finite Element Analysis is different than in FIG. 7. In FIG. 25, the scale is set to one-hundred and sixty megapascals (160 MPa), as that is the typical failure point for bone. Thus, the Finite Element Analysis of FIG. 25 illustrates the stresses created on framework 20 upon application of 10,000 N load, within a scale of one-hundred and sixty megapascals (160 MPa), to thereby illustrate where bone failure might occur anywhere along framework 20. As shown, certain areas of framework 20, illustrated in red, approach or exceed stresses of 160 MPa when a 10,000 N load is applied. Thus, at these areas, without resorbable component 50 and the support it provides for implant 10, there would likely be failure of vertebral bone and subsidence of framework 20 into the bone. In other words, these areas of high local stress on framework 20 (without resorbable component 50) would ordinarily result in framework 20 subsiding into the vertebral bodies.

Figure 24:
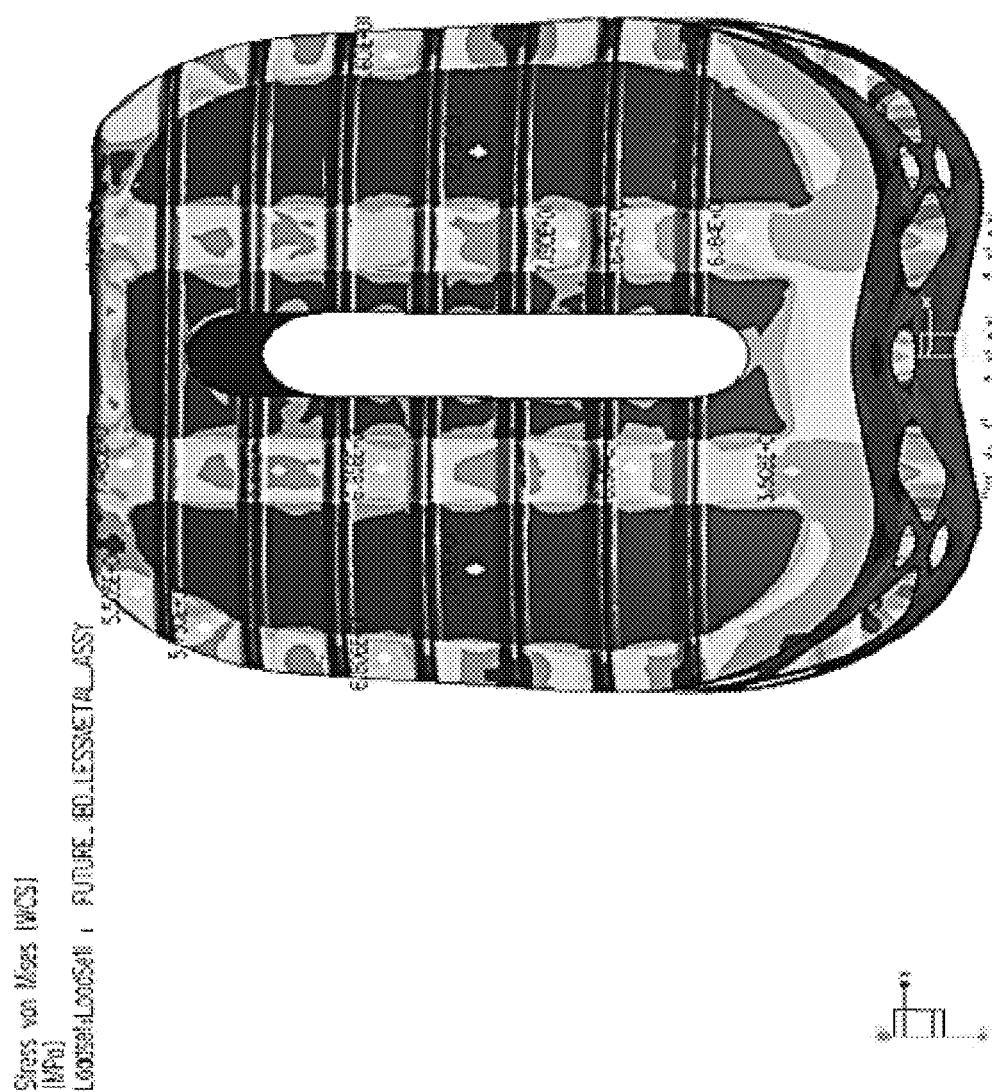
FIG. 24 is a Finite Element Analysis of a certain load being applied to the implant of FIGS. 1A-E, with the framework and resorbable component used therewith.

As seen in FIG. 24, however, which is a Finite Element Analysis of implant 10 (i.e., framework 20 with resorbable component 50), resorbable component 50 acts to distribute loads across the extent of implant 10 and thereby reduce the risk of subsidence. As shown, no areas on the top of implant 10 approach or exceed 160 MPa (the failure point for bone). Instead, maximum stresses across implant 10 appear to be on the order of about 60-80 MPa, and in an embodiment are 75 MPa. For the Finite Element Analyses of FIGS. 24-25, framework 20 was constructed as a scaffold of Ti6Al4V, having a Young's Modulus of about 104,800 MPa and Poison's Ratio of 0.3, while resorbable component was composed of a biologic material having a Young's Modulus of 4.1 GPa and Poison's Ratio of 0.25.

In a particular implementation of implant 10, the surface area of non-resorbable framework 20 may be about fifty percent (50%) of the surface area of the entire implant 10, while the surface area of resorbable component 50 may also be about fifty percent (50%). Further, the overall volume occupied by framework 20 may be about thirty percent (30%) of the volume of implant 10, while the overall volume of resorbable component 50 may be about seventy percent (70%). In this configuration, the 50%/50% surface area ratio results in a 68% reduction in the peak stress that the device imparts to the vertebral body endplate when a 10,000 N load is applied, which results in a stress (75 MPa) safely below the yield strength of bone (160 MPa). In the absence of resorbable component 50, the resulting stress to the vertebral endplate caused by framework 20 is about 237 MPa, which is well above the yield strength of bone and would be likely to result in unwanted subsidence of framework 20. Thus, the particular combination of framework 20 and resorbable component 50 acts to decrease subsidence of implant 10 and encourage or allow bone formation and fusion to occur.

Implant 10 may be implanted into a disc space between adjacent vertebral bodies or as part of a corpectomy procedure in the same fashion as a traditional interbody device (IBD) or vertebral body replacement (VBR), respectively. Implant 10 allows for fusion to occur as resorbable material 50 is resorbed and replaced by newly-formed bone. Non-resorbable framework 20 acts as a structural scaffold or as a framework for resorbable material 50 to interface with. The non-resorbable framework 20 that contacts the vertebral end plates can also act to help the fusion process by, for example, being osteoconductive and/or incorporating resorbable coatings or resorbable materials within voids or pores of the non-resorbable material, etc., as described above. The particular configuration of resorbable and non-resorbable material in implant 10 therefore efficiently achieves fusion and bone formation, while providing ample structural support for adjacent vertebral bodies.

A particular manufacturing technique may also be used to construct implant 10 of FIGS. 1A-E (or any of the other implants, discussed below). In an embodiment, polycaprolactone (PCL) is dissolved in Glacial Acetic Acid (GAA) at room temperature until homogenous. Bioactive glass is then added to the PCL-GAA solution under light agitation to prevent settling. Once thoroughly mixed, the solution is loaded into a syringe and extruded into a mold containing framework 20. The filled mold is then injected with water and/or completely submerged in a water bath to precipitate the plastic onto the device. Once all of the PCL has precipitated, the filled implant 10 is removed from the mold.

Referring to FIGS. 4A-E, an alternate implant 110 is shown that is similar to implant 10. Due to the similarities between implants 10, 110, like numerals (within the 100-series of numbers) refer to like elements in this embodiment and predominantly the differences between the embodiments will be discussed herein.

Implant 110 includes a structural, non-resorbable framework 120 and a resorbable component/material 150 positioned within and/or around framework 120. As shown in FIGS. 5A-E, framework 120 is similar to framework 20 of implant 10, except that it includes left 137, center 138, and right 139 sections and a keyed opening 144 between the sections. Keyed openings 144 are formed along top and bottom surfaces 122, 124 and extend from proximal end 140 to distal end 142 of framework 120. In a particular embodiment, a first keyed opening 144 is positioned along top surface 122 between left 137 and center 138 sections, a second keyed opening 144 is positioned along top surface 122 between center 138 and right 139 sections, a third keyed opening 144 is positioned along bottom surface 124 between left 137 and center 138 sections, and a fourth keyed opening 144 is positioned along bottom surface 124 between center 138 and right 139 sections. Thus, a total of four (4) keyed openings 144 may be present in an embodiment.

Keyed openings 144 are shaped and arranged to receive a variety of arrow-shaped bone anchors as disclosed, for example, in Applicant's U.S. Pat. No. 8,349,015, which is hereby incorporated by reference herein. An example of an arrow-shaped bone anchor is shown in FIGS. 4A-E as anchor 174. An anchor very similar to anchor 174 is shown and described in connection with FIGS. 6A-B of the '015 Patent, and it is expressly contemplated that anchor 174 may include any of the features of the anchor of FIGS. 6A-B of the '015 Patent, or any other anchor disclosed in the '015 Patent. Thus, anchor 174, for example and not by way of limitation, can include an interconnection portion 176 extending from an anchor portion 178 for engaging with keyed openings 144. Interconnection portion 176 may be dovetail-shaped in an embodiment to engage with a dovetail-shaped opening 144 in framework 120. Further, although not shown herein, as described in the '015 patent anchor 174 may have a stop feature at its trailing end to ensure that anchor 174 does not travel too far into framework 120. Anchor 174 may also have lock features for locking anchor 174 into engagement with framework 120 once fully inserted. Put simply, anchor 174 can include any of the features of any of the anchors of the '015 patent, and engage and be retained in framework 120 by the means described in the '015 patent. Anchor 174 can therefore provide an efficient means of securing implant 110 to adjacent vertebral bodies once implanted.

As shown in the particular implementation of anchor 174 in FIGS. 4A-E, anchors 174 may be arranged to diverge and angle away from one another along top and bottom surfaces 122, 124 of framework 120, and thus implant 110. However, any of the directional and/or angled configurations of anchors disclosed in the '015 patent could equally be used with framework 120, and thus implant 110.

Framework 120 also differs from framework 20 in that it is substantially devoid of struts and geometric openings, as present in framework 20. Instead, vertical openings 134 are defined in top and bottom surfaces 122, 124 of left 137, center 138, and right 139 sections of framework 120, and lateral openings 148 are present as well. Further, framework 120 may be open between each support column 132 within the main body of framework 120.

Resorbable component 150 is shown in detail in FIGS. 6A-E. As resorbable component 150 is somewhat similar to resorbable component 50, like numerals refer to like elements in this embodiment and predominantly the differences between components 50, 150 will be discussed herein. Resorbable component 150 includes left 168, center 170, and right 172 sections to match left 137, center 138, and right 139 sections of framework 120. Resorbable component 150 may be composed of a flowable material that is positioned within and/or around framework 120 during, for example, manufacturing. Alternatively, it may be possible to pre-construct resorbable component 150 and slide it into engagement with framework 120 through an opening in framework 120 (e.g., one of lateral openings 148). Each of left 168, center 170, and right 172 sections of resorbable component 150 include a vertical opening 160 that is alignable with vertical openings 134 of framework 120. Thus, once resorbable component 150 is positioned within and/or around framework 120, vertical openings 160 of resorbable component 150 define openings in implant 110 that, in an embodiment, are sized to receive bone-graft material (e.g., for promoting fusion).

Resorbable component 150 also includes its own keyed openings 166 for aligning with keyed openings 144 of framework 120 and providing an interconnection mechanism between implant 110 and anchors 174. In a particular embodiment, a first keyed opening 166 is positioned along top surface 152 of resorbable component 150 between left 168 and center 170 sections, a second keyed opening 166 is positioned along top surface 152 between center 170 and right 172 sections, a third keyed opening 166 is positioned along bottom surface 154 of resorbable component 150 between left 168 and center 170 sections, and a fourth keyed opening 166 is positioned along bottom surface 154 between center 170 and right 172 sections. Keyed openings 166, like keyed openings 144, may be of any shape, have any direction and/or angle, and include any of the features of such similar keyed openings as described in the '015 Patent, incorporated by reference above. Thus, keyed openings 166 engage with anchors 174 once resorbable component 150 is positioned within and/or around framework 120.

Resorbable component 150 may also include engagement structures 164, for example in the form of cutouts, arranged to engage with like engagement structures (not shown) in framework 120. Such engagement structures 164 secure resorbable component 150 to framework 120. Resorbable component 150 also includes an opening 180 for connection with an insertion tool that is alignable with like opening 136 in framework 120. Openings 136, 180 are, in an embodiment, threaded for engagement with a threaded portion of an implantation tool.

Although certain structures of framework 120 and/or resorbable component 150 are not discussed above, for example teeth 126, 162 thereon, it is to be understood that such structures are encompassed in framework 120 and/or resorbable component 150 and are referenced in the figures by way of reference numerals that correspond or are like the reference numerals for framework 20 and resorbable component 50 of implant 10. Additionally, it is to be understood that any of the materials disclosed for framework 20 and resorbable component 50 may be used to compose framework 120 and resorbable component 150, and that resorbable component can be used as a structural member in an embodiment or a non-structural member in other embodiments. When used as a structural member, resorbable component 150 can act to assist with preventing or mitigating subsidence of framework 120 into adjacent vertebral bodies, a common downfall of current PEEK and/or titanium cages. Further, the surface area and volume percentages and ratios discussed above in connection with implant 10 can also be used with implant 110.

Some beneficial aspects of implants 10, 110 above include but are not limited to: (1) the addition of a resorbable component 50, 150 that may, at least initially, act to distribute contact loads with bone in order to prevent failure of the bone due to high localized stresses (subsidence is a known potential failure mode of existing IBDs); (2) a particular balance of resorbable and non-resorbable structures that both meets overall implant structural requirements and results in minimizing the volume, location, and orientation of radiopaque non-resorbable structures to facilitate the use of radiographic imaging techniques to assess local anatomy and progress of a fusion mass; and/or (3) a combination of resorbable and non-resorbable regions able to interface with additional fixation elements in such a manner that fixation between the IBD and bone is not lost as material resorbs. Other benefits of implants 10, 110 are clearly also experienced.

FIGS. 8A-E depict another implant 210, according to an embodiment of the present invention. Implant 210 includes a substantially non-structural, non-resorbable frame 220 used in connection with a structural, resorbable component 250 positioned within frame 220. In this embodiment, certain like reference numerals refer to like elements but, due to the difference between implant 210 and implants 10, 110, no consistent numbering scheme is used.

Frame 220, as shown in FIGS. 9A-E, includes top and bottom bone-contacting surfaces 222, 224 that, in an embodiment, are formed of a porous but non-resorbable material. Top and bottom surfaces 222, 224 may be very thin in some instances (e.g., two millimeters (2 mm) or less), and thus, top and bottom surfaces 222, 224 alone are non-structural due to their thinness. Yet, when combined with structural resorbable component 250, implant 210 is able to meet the demands of the post-surgical loads that are typically experienced while also encouraging fusion and resorption.

Frame 220 also includes proximal and distal ends 240, 242 and an opening 236 for connection with an implantation tool (not shown) at proximal end 240. Opening 236 is threaded in an embodiment to engage with a threaded portion of an implantation tool (not shown). Frame 220 has a bulleted nose 238 at its distal end 242, and a vertical opening 226 through frame 220's top and bottom surfaces 222, 224. Frame 220 also includes a large lateral opening 228 sized to receive resorbable component 250, as described below. An opposing lateral side of frame 220 is closed, as shown in cross section in FIG. 9E.

FIGS. 10A-E show resorbable component 250 in various views. Resorbable component 250 may form a structural component for implant 210 and be composed of structural resorbable material. Any of the resorbable materials described in connection with implants 10, 110 can be used for resorbable component 250. Likewise, any of the materials and/or methods used to compose frameworks 20, 120 of implants 10, 110 can be used to construct frame 220 of implant 210.

Resorbable component 250 of FIGS. 10A-E includes top and bottom surfaces 252, 254, proximal and distal ends 256, 258, an implantation tool opening 266 in proximal end 256, and a bulleted nose 270 at distal end 258. A vertical opening 260 is also formed in resorbable component 250 through top and bottom surfaces 252, 254. In an embodiment, tool opening 266 is threaded for engagement with a threaded portion of an implantation tool (not shown). In addition, opening 266 may extend into the body of resorbable component 250 and open out into vertical opening 260, such that opening 266 may form an injection port for injection of a fusion material into the body of resorbable component 250. For instance, bone graft material may be injected into the body of resorbable component 250 through opening 266 so that such bone graft material is able to interface with adjacent vertebral bodies through vertical opening 260 and affect fusion. Resorbable component 250 also has engagement structures 264 that project outward from vertical opening 260. Engagement structures 264 may interface with like engagement structures (not shown) on frame 220 to secure resorbable component 250 relative to frame 220.

In use, resorbable component 250 may be slid into engagement with frame 220 through its lateral opening 228 so that engagement structures 264 of resorbable component 250 engage with like engagement structures (not shown) on frame 220 to secure resorbable component 250 relative to frame 220. Alternatively, these components could be pre-assembled by other means such as molding, packing, thermal assembly, 3D printing, or interference fit. With resorbable component 250 in frame 220, it can provide structural support for implant 210 and reinforce frame 220 (in particular frame 220's top and bottom bone-contacting surfaces 222, 224). Optionally, opening 266 in resorbable component 250 and opening 236 in frame 220 can be used as injection ports to inject a fusion material (e.g., bone graft) into resorbable component 250 for assisting with the fusion process. Since openings 236, 266 align once resorbable component 250 is positioned in frame 220, such openings 236, 266 may act as an injection port in the above-described manner. In this regard, the implantation tool (not shown) used to connect with openings 236, 266 and insert implant 210 into the intervertebral space may also have an injection conduit for injecting fusion material into resorbable component 250. Thus, the implantation tool (not shown) could threadably connect with at least one of openings 236, 266 and serve to also injection fusion material into resorbable component 250 through its injection conduit.

Although not shown, it is also contemplated that top and bottom surfaces 222, 224 of frame 220 and top and bottom surfaces 252, 254 of resorbable component 250 may be tapered towards one another to create a lordotic implant 210 for use in certain applications (e.g., in the lumbar spine where natural lordosis is present).

Implant 210, due to the thin top and bottom surfaces 222, 224 of frame 220 and the structural support provided by resorbable component 250, may also act to increase graft loading over time. As an example, as resorbable component 250 resorbs and new bone is formed, the structural stiffness of implant 210 may be reduced. In this case, where a bone graft is used with implant 210 (e.g., in vertical opening 260 of resorbable component 250 or elsewhere), such a decrease in stiffness can lead to increased graft loading over time and improve the fusion process.

In a particular embodiment, non-resorbable frame 220 may be composed of a titanium alloy and resorbable component 250 of a resorbable material with mechanical properties similar to bone, such as CLM. In this embodiment, non-resorbable frame 220 may occupy one-hundred percent (100%) of the overall surface area in contact with the vertebral endplates, while resorbable component 250 may occupy zero percent (0%). In this instance, the pores of non-resorbable frame 220 are not filled with a resorbable material. Further, the volume of frame 220 may be thirty six percent (36%) of the overall volume of implant 210, while the volume of resorbable component 250 may be sixty four percent (64%). A benefit of this volume ratio is that the overall stiffness of the device is primarily dictated by resorbable component 250, which makes up a majority of the volume and also bears a majority of the service load in the cephalad/caudad direction. Another benefit of this configuration, as it relates to implant 210, is that the radiopaque material (frame 220) has been located such that there is no obstruction for imaging the fusion mass from a lateral direction.

FIGS. 11A-E illustrate an implant 310, according to yet another embodiment of the present invention. Implant 310 comprises a non-resorbable, non-structural framework 320 that has a fluid channel conduit(s) 324 and a structural, resorbable component 350 positioned around framework 320. Due to the differences from previous embodiments, certain like numerals refer to like elements, but no consistent numbering scale is used in this embodiment.

As shown in FIGS. 12A-E, framework 320 of implant 310 has a main body 322 that includes at least one conduit 324 therein. Framework 320 also has proximal and distal ends 330, 332, an injection port 334 at proximal end 330, and a vertical opening 336 through main body 322. Injection port 334 doubles as an implantation tool opening, and thus, it is threaded in an embodiment to engage with a threaded portion of an implantation tool (not shown). Injection port 334 is fluidly connected to conduit 324 so that fluid can be injected into port 334 and travel into and through conduit 324. In an embodiment, conduit 324 traverses substantially an entire perimeter of main body 322 of framework 320. Framework 320 also includes an enlarged portion 340 forming a step at its proximal end 330 and conduit 324 may traverse enlarged portion 340 until it intersects with and opens out into injection port 334. In a particular embodiment, main body 322 is closed beyond injection port 334 so that, as fluid is forced into injection port 334, it flows from port 334 and into conduit 324.

In another embodiment, injection port 334 and conduit 324 can include any of the fittings and/or flow channels described in connection with Applicant's U.S. Application Ser. No. 62/103,270, now U.S. patent application Ser. No. 14/994,697, which are hereby incorporated by reference herein. The '270 Application was attached as Exhibit B to the '146 Provisional. As an example, FIGS. 5A-E of the '270 Application depict an implant 410 with a threaded passage 424 and a flow channel 428 in fluid communication therewith. The structure of threaded passage 424 and flow channel 428 could be utilized in connection with framework 320 herein. Indeed, although not expressly described in this disclosure, it is to be appreciated that any of the flow channels (including multiple flow channels), fittings, passages therefor, and other structures of the implants taught in the '270 Applicant can be used with framework 320 and/or resorbable component 350 herein. Applicant provides certain examples of the structures from the '270 Application that could be used herein, but such examples are not to be taken as limiting and it should be recognized that any of the principles of the '270 Application are usable with implant 310.

Framework 320 of implant 310 also has a plurality of cylinders 326 projecting outward from main body 322, which terminate in holes 327. As described in more detail below, cylinders 326 extend through resorbable component 350 so that holes 327 are open to the exterior of implant 310, much like the holes described in the '270 application. As shown in cross section in FIG. 12E, cylinders 326 each have a conduit 338 that is in fluid communication with conduit 324 of main body 322. Thus, fluid can flow from conduit 324, into each of conduits 338 of cylinders 326, and ultimately to the exterior of implant 310 via holes 327. As such, it is possible to inject fluid into implant 310 and have the fluid coat the exterior of implant 310. As described in the '270 application, the fluid injected into implant 310 may be a biologic material, a therapeutic material, a bone cement, bone-growth promoting material, Bone Marrow Aspirate, antimicrobial material, bone morphogenic proteins ("BMP"), stem cells, solutions to assist in the resorption process, tissue-targeted glycosaminoglycans, or any other like material.

Resorbable component 350, one side of which is shown in FIGS. 13A-E, includes top and bottom surfaces 352, 354, proximal and distal ends 356, 358, a vertical opening 360, and teeth 362 formed on top surface 352. Resorbable component 350 may be composed of any of the resorbable materials discussed in connection with the previous implants 10, 110, 210 and, in an embodiment, is a flowable material that is embedded within framework 320 during manufacturing. In this regard, framework 320 and its projecting cylinders 326 can act as a scaffold to retain resorbable component 350 in connection with framework 320. Additionally, framework 320, in its capacity as a scaffold, can provide support to resorbable component 350 so that component 350 does not crack or fracture during implantation. Indeed, resorbable materials are, in some existing implants, susceptible to fracture or cracking during implantation. As an example, allograft bone is often brittle during implantation.

Resorbable component 350 also has a series of holes 368 arranged to align with projecting cylinders 326 of framework 320 and allow fluid to exit holes 327 of such cylinders 326. Fluid exiting holes 327 of cylinders 326 (and thus holes 368 of resorbable component 350) may act to coat top surface 352 of resorbable component 350 and assist with the resorption and/or fusion process. Resorbable component 350 further includes, at its proximal end 356, a stepped portion 364 shaped and arranged to engage with enlarged portion 340 of framework 320. Although not shown, a second resorbable component 350 identical to that shown in FIGS. 13A-E is usable with implant 310 on an opposing side of implant 310.

While not described above, it is also contemplated that conduit 324 of framework 320 may, in addition to or as a substitute to directing fluid to an exterior of implant 310, also be arranged to direct fluid to a location fully enclosed within resorbable component 350. Such a conduit would be beneficial to deliver fluid (e.g., a resorptive-enhancing fluid) to a location within resorbable component 350. It is also the case that conduit 324 (or multiple conduits if included) may direct fluid to other exterior parts of implant 310, for example the sides or proximal and/or distal ends of implant 310. In addition, if multiple conduits 324 are included with framework 320, different materials can be directed to different portions of implant 310. These types of conduits are disclosed in more detail in the '270 application.

FIGS. 14A-E depict an implant 410, according to another embodiment of the present invention. Implant 410 includes a non-structural, non-resorbable framework 420 and a structural, resorbable component 450 positioned within and/or around framework 420. Due to the differences from previous embodiments, certain like numerals refer to like elements, but no consistent numbering scale is used in this embodiment.

As shown in FIGS. 15A-E, framework 420 has first and second ring members 422, 424 and struts 426 that connect ring members 422, 424. Struts 426 terminate in proximal and distal end plates 428, 430 arranged on framework 420. In an embodiment, proximal end plate 428 includes an implantation tool opening 432 that is optionally threaded for engagement with a threaded portion of an implantation tool (not shown). Framework 420, via its ring members 422, 424, struts 426, and end plates 428, 430, provides a scaffold for embedding resorbable component 450 within framework 420. Although framework 420 is non-structural, in the sense that it does not support post-surgical loads directly, it provides strength and rigidity to implant 410 and resorbable component 450 thereof.

Resorbable component 450 is shown in FIGS. 16A-E and includes a main body 451 having top and bottom bone-contacting surfaces 452, 454, proximal and distal ends 456, 458, an implantation tool opening 466 at proximal end 456, and a vertical opening 460 formed through main body 451. As with the previous embodiments, implantation tool opening 466 may or may not be threaded for engagement with a threaded portion of an implantation tool (not shown). Additionally, opening 466 may be in fluid communication with vertical opening 460 so that a fusion or another biologic material can be injected into opening 460 via a tool. Such a tool is disclosed, for example, in the '270 Application and it is expressly contemplated that any tool of the '270 Application is usable with implant 410, as well as any of the previous implants.

Resorbable component 450 also includes teeth 462 on its top and bottom surfaces 452, 454, and may be composed of any of the resorbable materials hereinbefore described. In an embodiment, resorbable component 450 is preassembled on framework 420 at the point of manufacture and provides structural support for implant 410 in that it is capable of supporting the post-surgical loads borne on implant 410 after insertion into a patient. This type of implant configuration is particularly useful when the resorbable material is strong but brittle, as spinal implants are often impacted into place and must be able to withstand impact loads without fracturing or becoming damaged. With implant 410, impaction loads are borne by framework 420 (e.g., at tool opening 432/proximal end plate 428), and thus, the resorbable material of resorbable component 450 is safe from fracture and/or other damage during implantation. Resorbable component 450 also resists fracture due to the support provided by framework 420 in its capacity as a scaffold.

Figure 17:
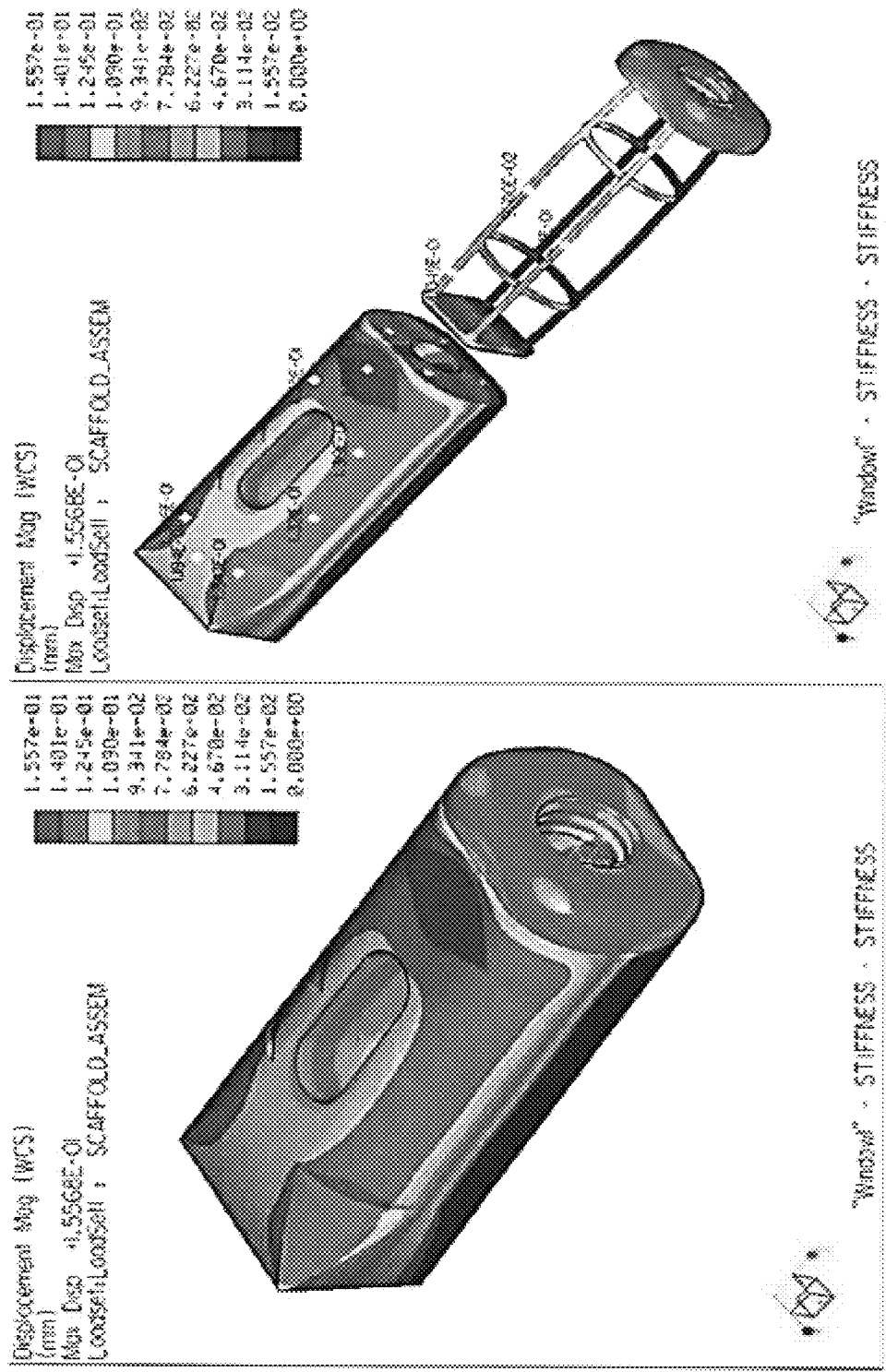
FIGS. 17-18 are Finite Element Analyses of the implant of FIGS. 14A-E.
Figure 18:
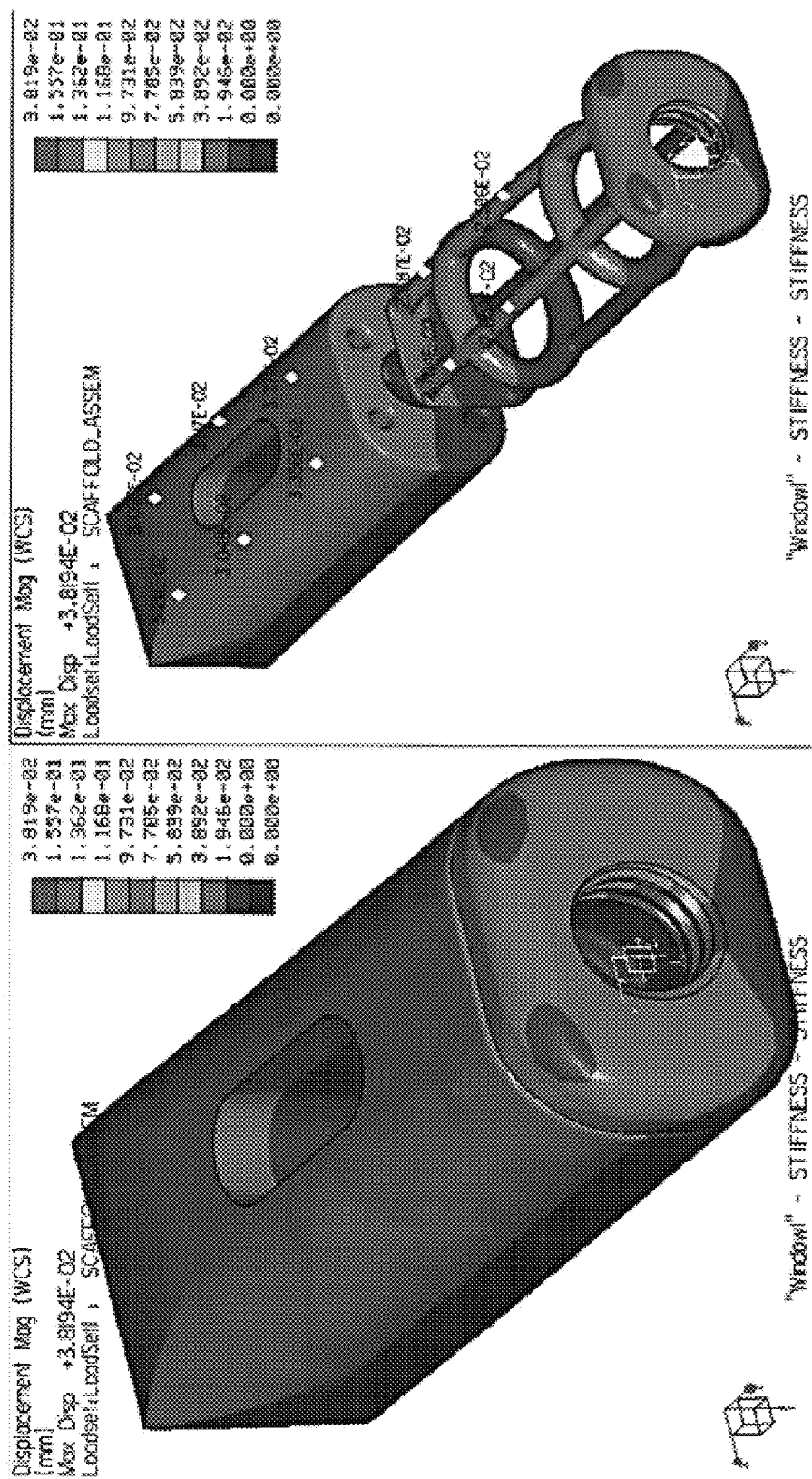
Figure 19:
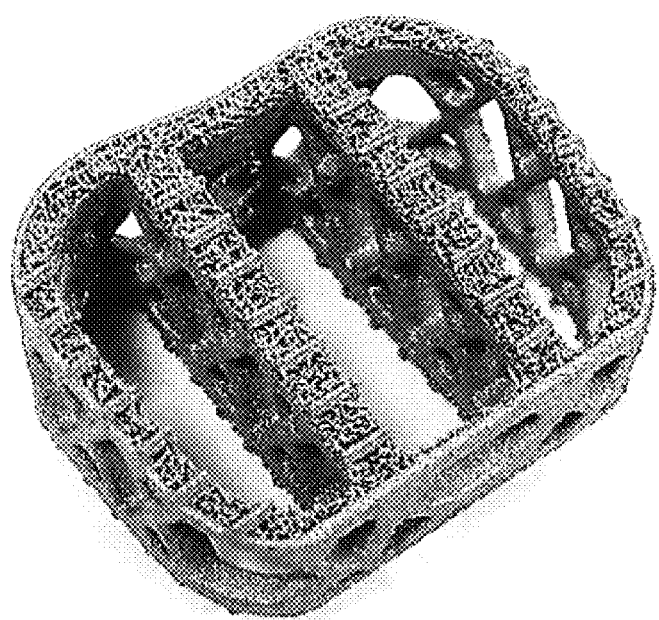
FIG. 19 is a perspective view of a prototype embodying the non-resorbable, structural framework of the implant of FIGS. 1A-E.
Figure 20:
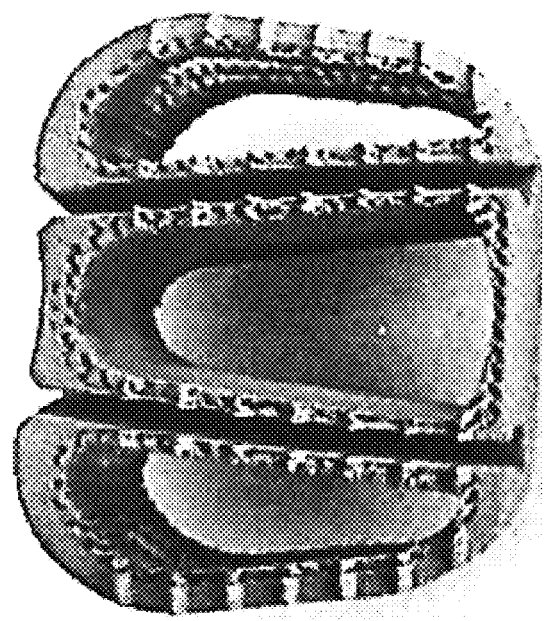
FIG. 20 is a perspective view of a prototype embodying the non-resorbable, structural framework of the implant of FIGS. 4A-E.

In a particular embodiment, it is possible to modify framework 450 to also increase or decrease the overall stiffness of implant 410. As an example, the components of framework 420 may be made thicker or thinner in certain locations (e.g., struts 426 and rings 422, 424) to increase or decrease the overall rigidity of framework 420, and thus implant 410. Different thickness frameworks 420, and Finite Element Analyses related thereto, are shown in FIGS. 17-18. As reflected in those figures, a different stiffness is realized for implant 410 between the thicker and thinner frameworks 420.

FIGS. 19-23 depict various images of prototypes of frameworks 20, 120, 220, 320, 420 of implants 10, 110, 210, 310, 410. It is to be understood that any of these prototypes can be constructed using an additive manufacturing process, as hereinbefore disclosed. Additionally, each of the frameworks may be composed of any of the materials discussed in connection with any of the above-described frameworks. Further, other manufacturing methods such as injection molding processes may be used to construct frameworks 20, 120, 220, 320, 420. Thus, a variety of materials and manufacturing methods may be utilized to create frameworks 20, 120, 220, 320, 420. Certain particular features of the various prototypes will now be discussed.

Referring to all of the prototypes of FIGS. 19-23, it is seen that a porous and/or roughened layer or surface coating may be used on all, substantially all, or a majority of the exposed surfaces of frameworks 20, 120, 220, 320, 420. Such a coating could enhance the resorptive and/or fusion characteristics of a particular framework, make it more amenable to connection with a particular resorbable component or material, or simply increase the framework's resistance to migration in the intervertebral space once implanted.

Figure 21:
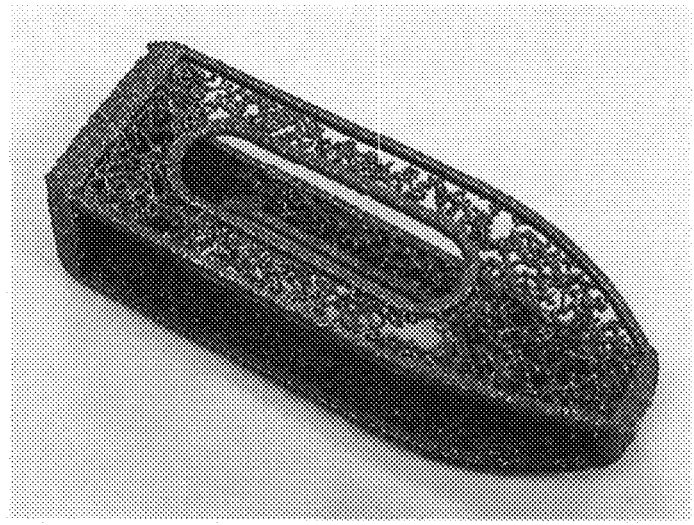
FIG. 21 is a perspective view of a prototype embodying the porous, non-resorbable framework of the implant of FIGS. 8A-E.
Figure 22:
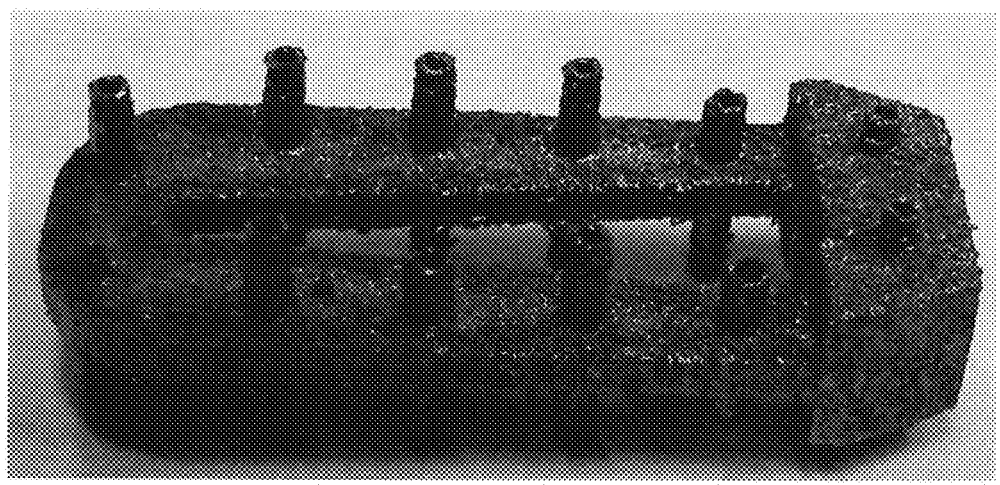
FIG. 22 is a perspective view of a prototype embodying the non-resorbable framework of the implant of FIGS. 11A-E.

Referring to the prototype of framework 220 of FIG. 21, it is also seen that top and bottom bone-contacting surfaces 222, 224 are highly porous and thin. Such surfaces 222, 224, as described above, are structurally supported by resorbable component 250. Additionally, in the image of the prototype of framework 220, it is shown that framework 220 can have multiple lateral openings for receiving resorbable component 250, instead of only a single lateral opening 228.

Figure 23:
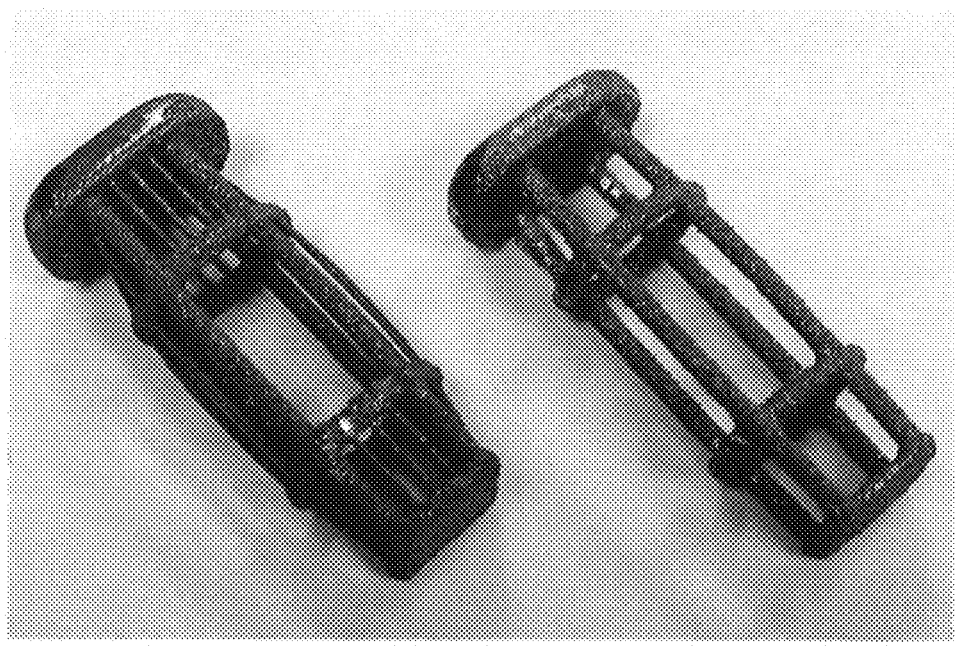
FIG. 23 is a perspective view of several prototypes embodying the non-structural, non-resorbable framework of the implant of FIGS. 14A-E.

Turning to the prototype of framework 420 of FIG. 23, it is shown in one of the prototypes (left) that a variety of differently-sized struts may be used in framework 420. As an example, smaller struts may traverse between distal end plate 430 and second ring 424 and between proximal end plate 428 and first ring 422. One or more side struts may also be used on framework 420, as shown. Such side struts may be bowed and be connected to proximal end plate 428, first ring 422, second ring 424, and finally distal end plate 430. These additional struts may provide yet additional stiffness to implant 410 and/or act as a further scaffold for resorbable component 450.

A surgical kit is also contemplated within the present invention. Due to the inability for many of the known resorbable materials to be properly sterilized via autoclave without being rendered unusable, it is expected that at least any of the resorbable components described above may be provided in a sterile package in the kit. This packaging could enclose either the entire finished implant (resorbable and non-resorbable components), or just the resorbable component with the intent to assemble intraoperatively. Indeed, although many of the implants discussed above are described as being assembled upon manufacturing, it is contemplated that resorbable and non-resorbable components of the above implants may be assembled in the operating room or in-situ. The in-situ assembly process could include first implanting the non-resorbable component into the spine, and then injecting or flowing a curable resorbable component through and/or around the non-resorbable portion/framework within the disc space. The resorbable component could then be allowed to cure/harden, at which point the implant may be left implanted for purposes of resorption of the resorbable material and fusion of the vertebral bodies. It is contemplated that such a process is possible with any of frameworks 20, 120, 220, 320, 420 of implants 10, 110, 210, 310, 410.

The surgical kit may also include implants 10, 110, 210, 310, 410 of different sizes for use with different patients, and tools for the implantation of such implants. An example of such a tool is the tool disclosed in the '270 application, which is usable to insert some of the implants described previously and/or inject a biologic material into such implants.

Additionally, while no particular surgical approach has been discussed above in connection with implants 10, 110, 210, 310, 410, and such implants are not limited to any particular surgical approach or use, it is contemplated that certain of the above implants may be more particularly suited for certain surgical applications. As an example, implants 10, 110 may be suited for use as ALIF implants (anterior lumbar interbody fusion), implant 210 may be suited for use as a PLIF implant (posterior lumbar interbody fusion), and implants 310, 410 may be suited for use as DLIF implants (direct lateral interbody fusion). Of course, the foregoing implants may be suitable for use in other areas of the spine and along different surgical approaches (e.g., anterolateral, transforaminal, etc.). As an example, the features and structures of the above implants may be suitable for use in cervical applications. The above-described uses and surgical approaches are therefore not to be taken as limiting and are merely exemplary. Likewise, the implants shown in the figures are merely examples of those which can be created according to the present invention. It is contemplated that other implant shapes/configurations can be made in accordance with the present invention.

In the devices shown in the figures, particular structures are shown as being adapted for use in the implantation of an implant according to the present invention. The invention also contemplates the use of any alternative structures for such purposes, including structures having different lengths, shapes, and/or configurations. For instance, although threaded connection mechanisms are taught herein (e.g., for insertion of the foregoing implants with an implantation tool), it is equally the case that non-threaded connection mechanisms can be used. For instance, a bayonetted connection, press-fit connection acting through dimensional interferences, luer connection, or other like locking connection may be used to implant any of implants 10, 110, 210, 310, 410 into the intervertebral space via an implantation tool with a like connection. This is particularly the case for implant 310 which, although it has a threaded, recessed opening 334, may alternatively include any of the projecting luer fittings disclosed in the '270 Application. Implant 310 is, of course, merely used as an example.

Further modifications and variants of the foregoing implants 10, 110, 210, 310, 410 are also contemplated. For instance, although certain of implants 10, 110, 210, 310, 410 may not be described above as including lordotic bone-contacting surfaces, such a feature is expressly contemplated with each of implants 10, 110, 210, 310, 410 as an option. In particular, it is contemplated that any of implants 10, 110, 210, 310, 410 may include lordotic surfaces (e.g., surfaces that taper towards one another) to accommodate natural lordosis that is present in certain areas of the spine. Some of implants 10, 110, 210, 310, 410 are shown in the figures with a lordotic taper, although that feature may not be expressly discussed above.

In addition, while discussed somewhat in connection with implant 310, it is contemplated that such implant 310 may include multiple fluid conduits instead of the single conduit 324 shown in the figures. Such conduits may be fluidly isolated from one another to allow different fluids to be transferred to different parts of the implant, or the conduits may be fluidly connected. Additionally, certain fluid conduits may lead to areas wholly encompassed in resorbable component 350 instead of opening out to an exterior of implant 310, as described above. Some of these and other features are taught in the '270 Application, and it is to be understood that such features and/or structures are usable with implant 310.

In a further example, although implant 110 is described as using a particular bone anchor 174, it is contemplated that framework 120 and resorbable component 150 may be provided with more traditional bone-anchor features. For instance, framework 120 and resorbable component 150 may be provided with threaded holes for engaging with traditional threaded bone screws. Such holes may be arranged substantially as shown in connection with keyed openings 144, 166 (e.g., the holes may number four (4) in total, and diverge outward so that bone screws are directed up/down into the vertebral bodies, and in an outward direction). If bone-screw holes are included, certain anti-backout features might also be provided. For instance, a movable protrusion may be provided in each hole that automatically moves in response to a bone screw being inserted into the hole, and snaps back once the bone screw has passed the protrusion so as to cover the particular bone screw. Such a mechanism could prevent backout of screws inserted into implant 110. Other anti-backout mechanisms might also be used, such as traditional "man-hole covers," which are attached to the implant after the bone screws have been inserted and act to cover one or more of the bone screws.

In further variants, it is contemplated that any of implants 10, 110, 210, 310, 410 may utilize the following surface area and/or volume ranges for the non-resorbable and resorbable components thereof:

|  | Surface Area in Contact with Endplates | | Volume | |
| --- | --- | --- | --- | --- |
|  | Minimum | Maximum | Minimum | Maximum |
| Non-resorbable | 10% | 100% | 10% | 80% |
| Resorbable | 0% | 90% | 20% | 90% |

As yet another example, any of the resorbable components above may be combined with biologics and/or anti-infectives, including but not limited to bone marrow, blood, growth factors, proteins, peptides CAGs, antimicrobials, and/or antibiotics.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

It will also be appreciated that the various dependent claims and the features set forth therein can be combined in different ways than presented in the initial claims. In particular, any feature of any dependent claim may be combined with a feature of another independent or dependent claim, to the extent technologically feasible, as if the claims were written with multiple dependencies to reflect such different combinations. It will further be appreciated that the features described in connection with individual embodiments may be shared with others of the described embodiments.

The invention claimed is:

1. An implant sized and adapted for insertion into an intervertebral space between adjacent vertebral bodies comprising:
    a non-structural, non-resorbable framework having a main body and a first fluid conduit within the main body, the main body having an injection port in fluid communication with the first fluid conduit;
    a resorbable, structural component having top and bottom bone-contacting surfaces and an opening in at least one of the top and bottom surfaces, the opening being in fluid communication with the first fluid conduit, and a second fluid conduit projecting outward from the main body and being fluidly connected with the first fluid conduit in the main body, wherein the outwardly-projecting second fluid conduit defines the opening in the at least one of the top and bottom surfaces of the resorbable, structural component.

2. An implant according to claim 1, wherein the resorbable, structural component is a multi-piece component.

3. An implant according to claim 1, wherein the resorbable, structural component surrounds the outwardly-projecting fluid conduit.

4. An implant according to claim 1, wherein a vertical opening extends through the main body of the framework.

5. A method of using an implant comprising:
  implanting an implant between adjacent vertebral bodies, the implant being sized and adapted for insertion into an intervertebral space between adjacent vertebral bodies, the implant comprising a non-structural, non-resorbable framework having a main body and a fluid conduit within the main body, the main body having an injection port in fluid communication with the fluid conduit, the implant including a resorbable, structural component having top and bottom bone-contacting surfaces and an opening in at least one of the top and bottom surfaces, the opening being in fluid communication with the fluid conduit, and
  injecting a biologic material into the injection port so that the biologic material travels through the fluid conduit in the main body and out of the opening in the at least one of the top and bottom surfaces of the resorbable, structural component.

6. The method according to claim 5, wherein the biologic material is selected from the group consisting of a bone cement, bone-growth promoting material, Bone Marrow Aspirate, antimicrobial material, bone morphogenic proteins ("BMP"), stem cells, solutions to assist in the resorption process, and tissue-targeted glycosaminoglycans.

* * * * *